(12) United States Patent
Bao

(10) Patent No.: US 9,867,889 B2
(45) Date of Patent: Jan. 16, 2018

(54) SHAPE-CONTROLLED MAGNETIC NANOPARTICLES AS T1 CONTRAST AGENTS FOR MAGNETIC RESONANCE IMAGING

(75) Inventor: Yuping Y. Bao, Tuscaloosa, AL (US)

(73) Assignee: The Board of Trustees of the University of Alabama, Tuscaloosa, AL (US)

( * ) Notice: Subject to any disclaimer, the term of this patent is extended or adjusted under 35 U.S.C. 154(b) by 279 days.

(21) Appl. No.: 13/821,100

(22) PCT Filed: Sep. 26, 2011

(86) PCT No.: PCT/US2011/053268
§ 371 (c)(1),
(2), (4) Date: Mar. 6, 2013

(87) PCT Pub. No.: WO2012/050810
PCT Pub. Date: Apr. 19, 2012

(65) Prior Publication Data
US 2013/0177503 A1   Jul. 11, 2013

Related U.S. Application Data

(60) Provisional application No. 61/387,639, filed on Sep. 29, 2010.

(51) Int. Cl.
*A61K 49/18* (2006.01)

(52) U.S. Cl.
CPC ...... *A61K 49/1839* (2013.01); *A61K 49/1833* (2013.01); *A61K 49/1854* (2013.01); *A61K 49/1857* (2013.01); *Y10T 428/2982* (2015.01)

(58) Field of Classification Search
CPC ............ A61K 49/1833; A61K 49/1839; A61K 49/1857; A61K 49/1854; Y10T 428/2982
See application file for complete search history.

(56) References Cited

U.S. PATENT DOCUMENTS

| | | |
|---|---|---|
| 2005/0130167 A1 | 6/2005 | Bao et al. |
| 2005/0260137 A1 | 11/2005 | Acar |
| 2006/0211152 A1 | 9/2006 | Peng |
| 2006/0233712 A1 | 10/2006 | Penades et al. |
| 2009/0032781 A1* | 2/2009 | Wang et al. ............. 252/521.2 |
| 2009/0247652 A1 | 10/2009 | Silverman et al. |
| 2010/0008854 A1 | 1/2010 | Haam |
| 2010/0303730 A1* | 12/2010 | Hegmann et al. ......... 424/9.32 |

FOREIGN PATENT DOCUMENTS

| | | |
|---|---|---|
| WO | 2006025627 A1 | 3/2006 |
| WO | 2007069040 A2 | 6/2007 |
| WO | 2007097593 A1 | 8/2007 |
| WO | 2009135937 A2 | 11/2009 |
| WO | 2009136763 A2 | 11/2009 |

OTHER PUBLICATIONS

The International Search Report and Written Opinion dated Jun. 1, 2012.
Huang, et al., "Investiation of Growth Mechanism of Iron Oxide Nanoparticles Via Seed-Mediated Method and its Cytoxicity Studies," J. Phys. Chem. C. 2008, vol. 112, pp. 15684-15690.
Thomson, Jordan W., et al., Ultrathin Bi 2 S 3 Nanowires: Surface and Core Structure at the Cluster-Nanocrystal Transition, Journal of the American Chemical Society vol. 132, No. 26, Jul. 7, 2010, pp. 9058-9068.
European Search Report and Written Opinion for Application No. EP 11 83 3000 of Jul. 15, 2016.

* cited by examiner

*Primary Examiner* — Robert Cabral
(74) *Attorney, Agent, or Firm* — Thomas | Horstemeyer, LLP

(57) ABSTRACT

Methods are provided for the generation of nanostructures suitable for use in magnetic resonance imaging where the nanostructures have at least one dimension of about 2 nm or less. In particular, the methods comprise the selective use of incubation temperatures that result in the controlled removal of ligands from metallic cores to which they are attached, allowing the metallic cores or the precursor moieties to unite to form nanostructures of defined and predictable shapes, but having at least one dimension significantly less that at least one other dimension. Accordingly, the nanostructures of the disclosure may be ultrathin sheets, rods, whiskers and the like, or even structures that are thin and porous resembling rice grains. The temperatures useful in the methods of the disclosure are less than 300° C. and allow for progressive elevation of the incubation temperature. The methods are especially advantageous for synthesizing nanoparticles that may be administered to an animal or human subject for imaging with magnetic resonance. Accordingly, the nanostructures of the disclosure comprise a metallic core, most typically, but not necessarily limited to, a ferrite moiety that can be a ferrous or ferric ion alone or in combination with other metallic elements. However, the methods of the disclosure are also suitable for generating nanostructures with non-ferrous cores such as magnesium or manganese cores.

25 Claims, 33 Drawing Sheets

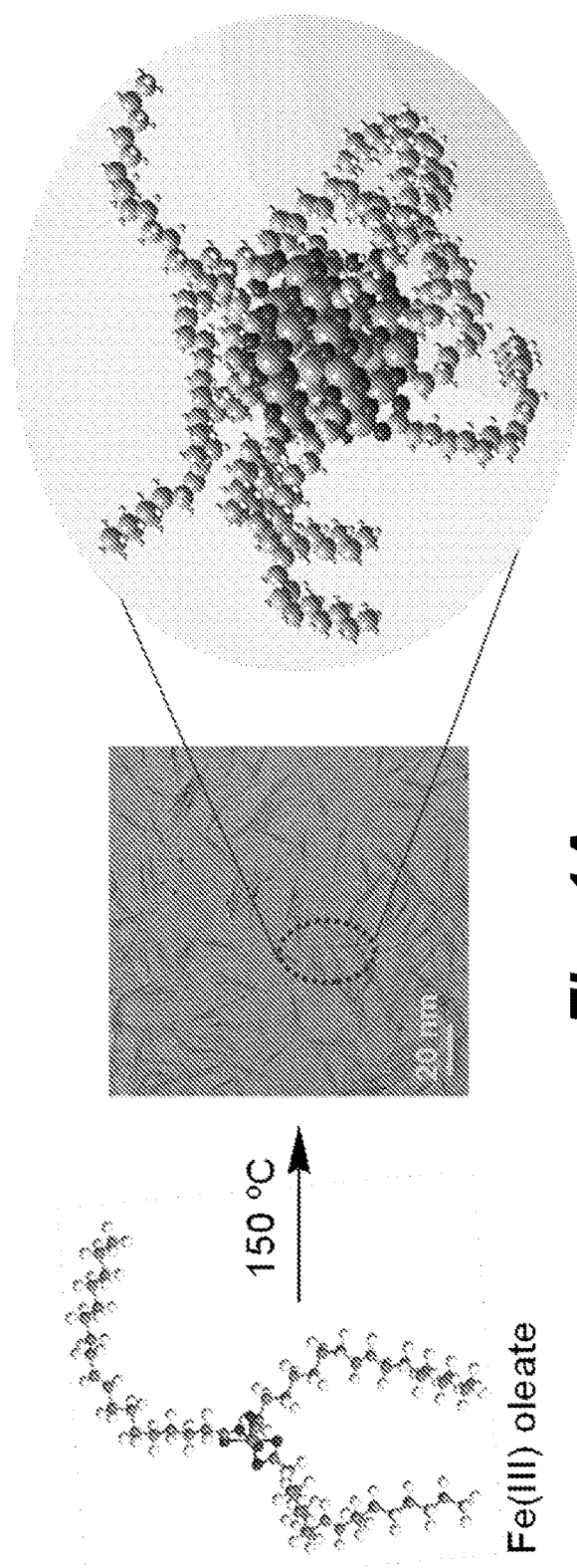

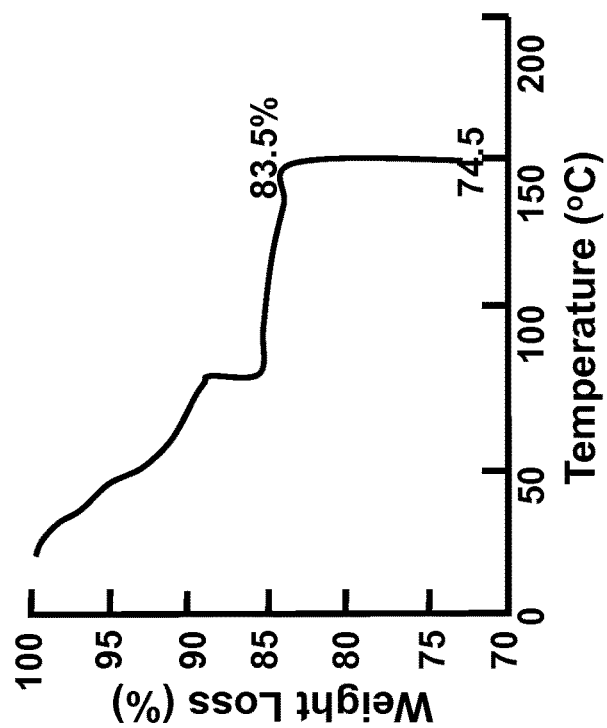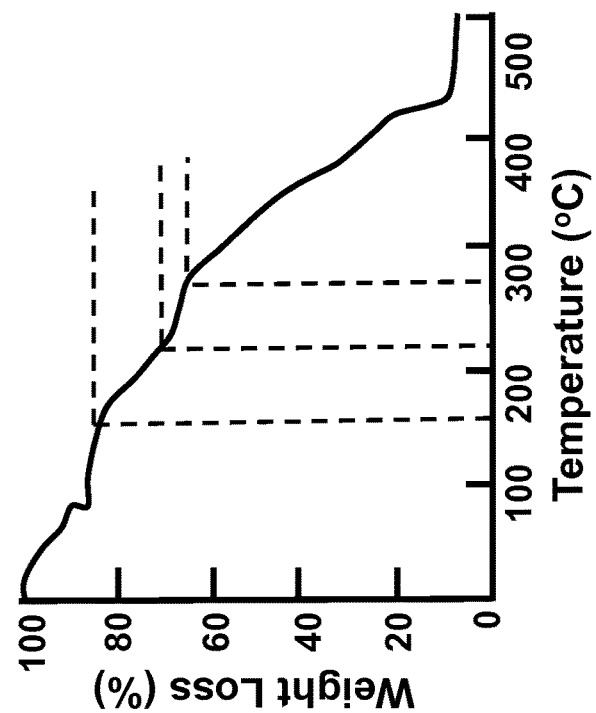

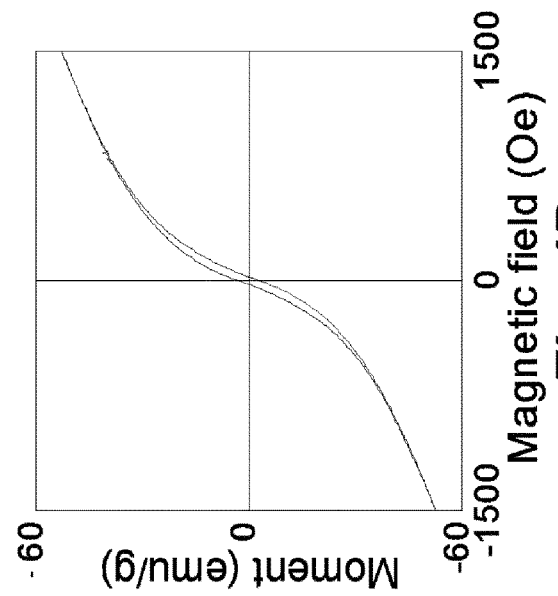
Fig. 4A
Fig. 4B

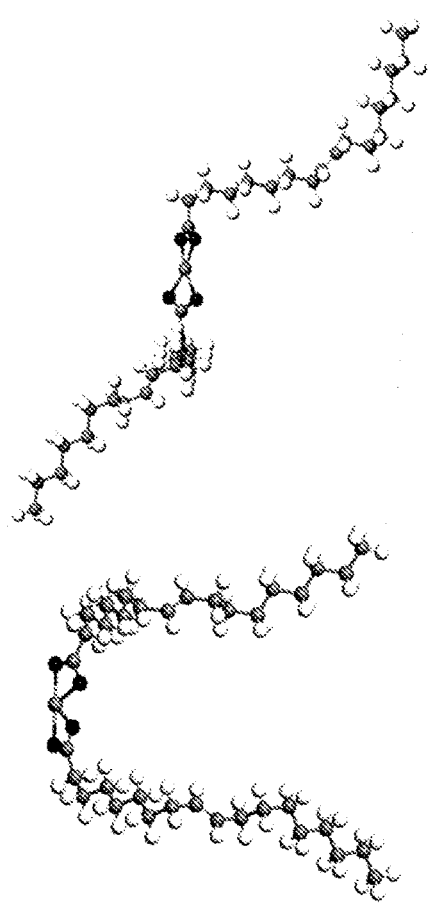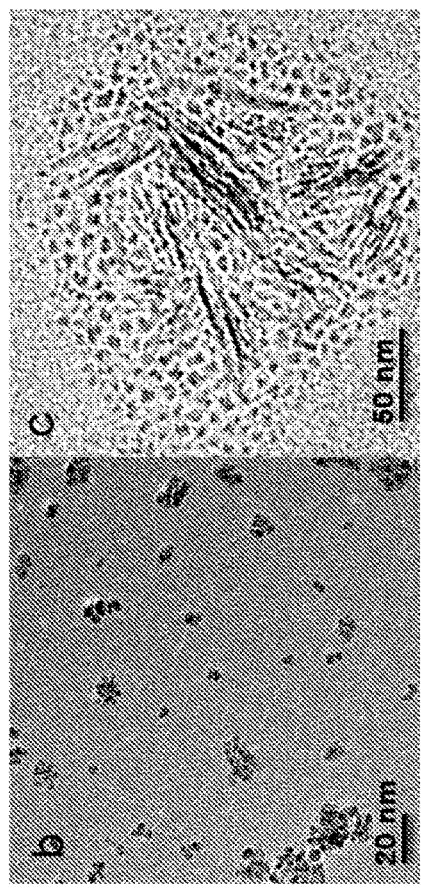
Fig. 6A
Fig. 6B
Fig. 6C

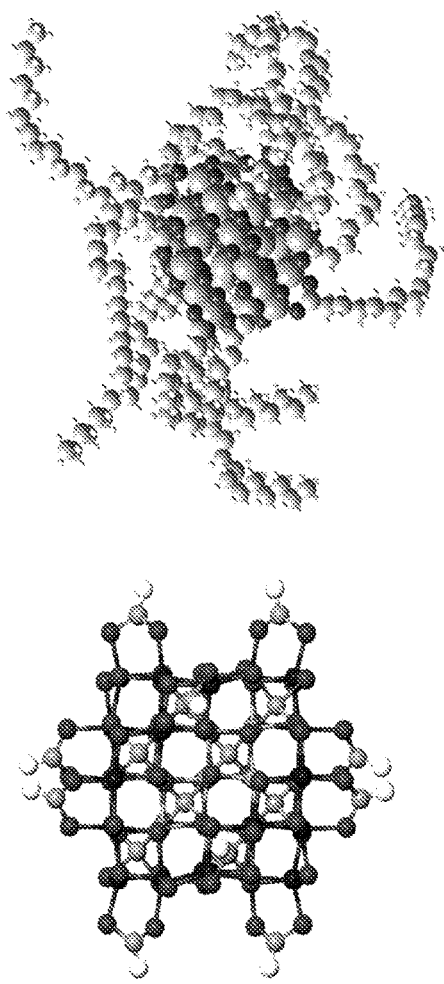
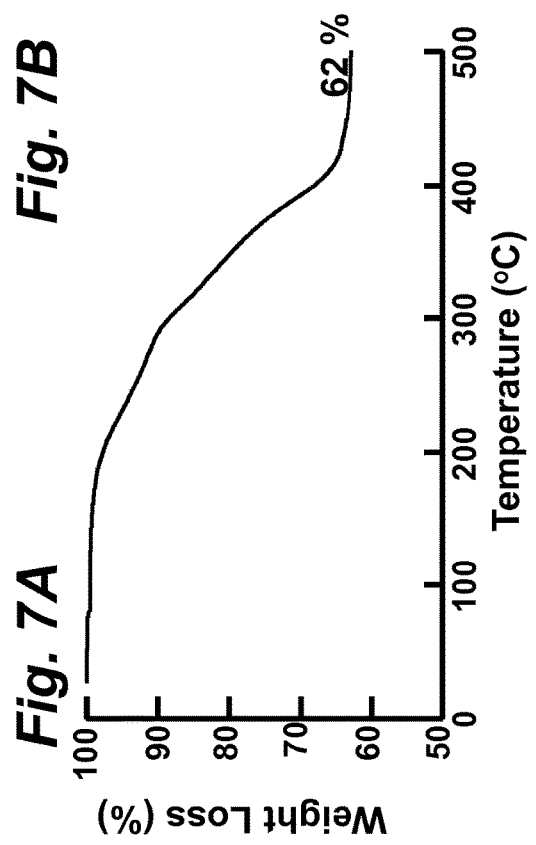
Fig. 7A
Fig. 7B
Fig. 7C

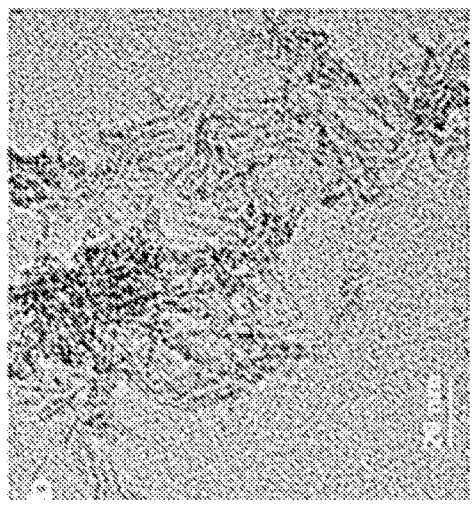
Fig. 9B
Fig. 9A
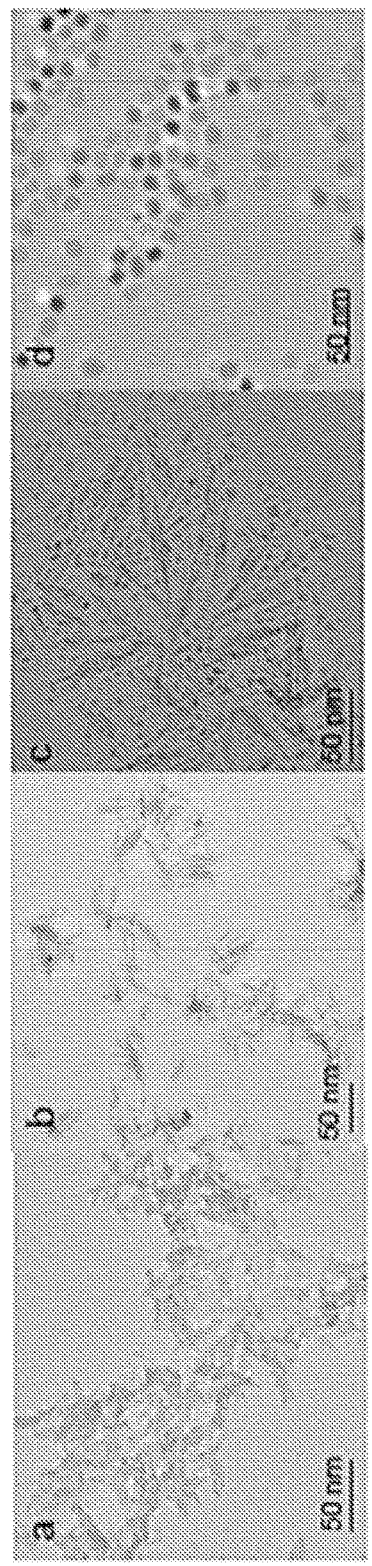
Fig. 10D
Fig. 10C
Fig. 10B
Fig. 10A

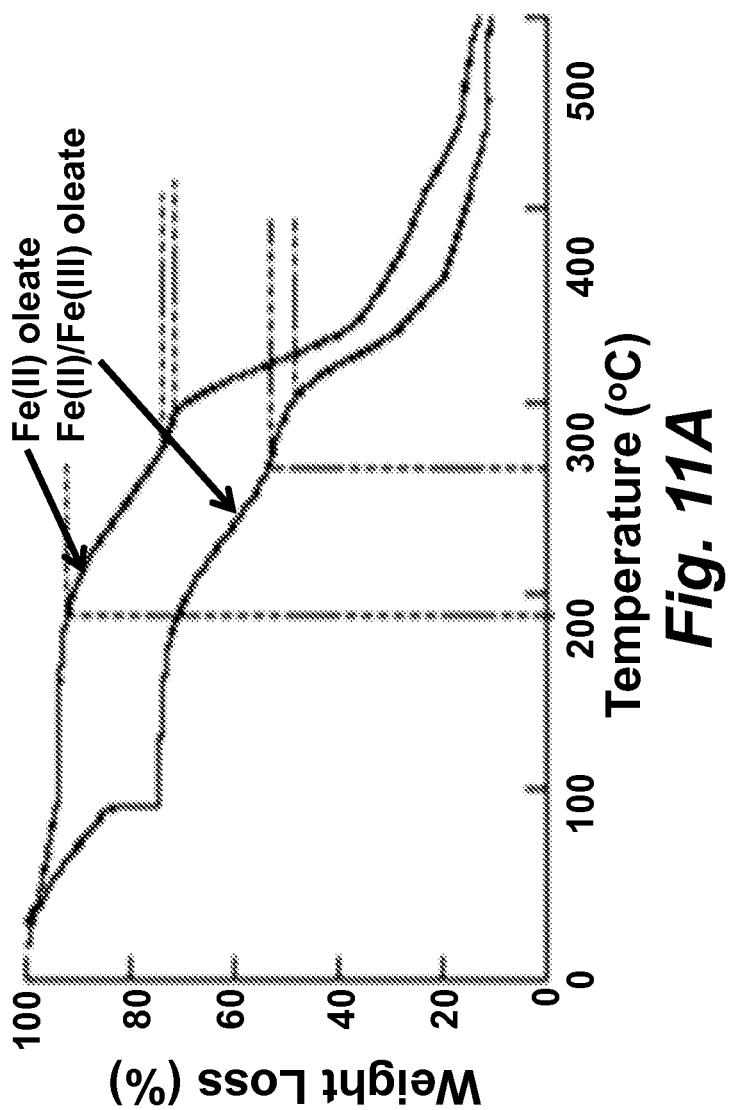

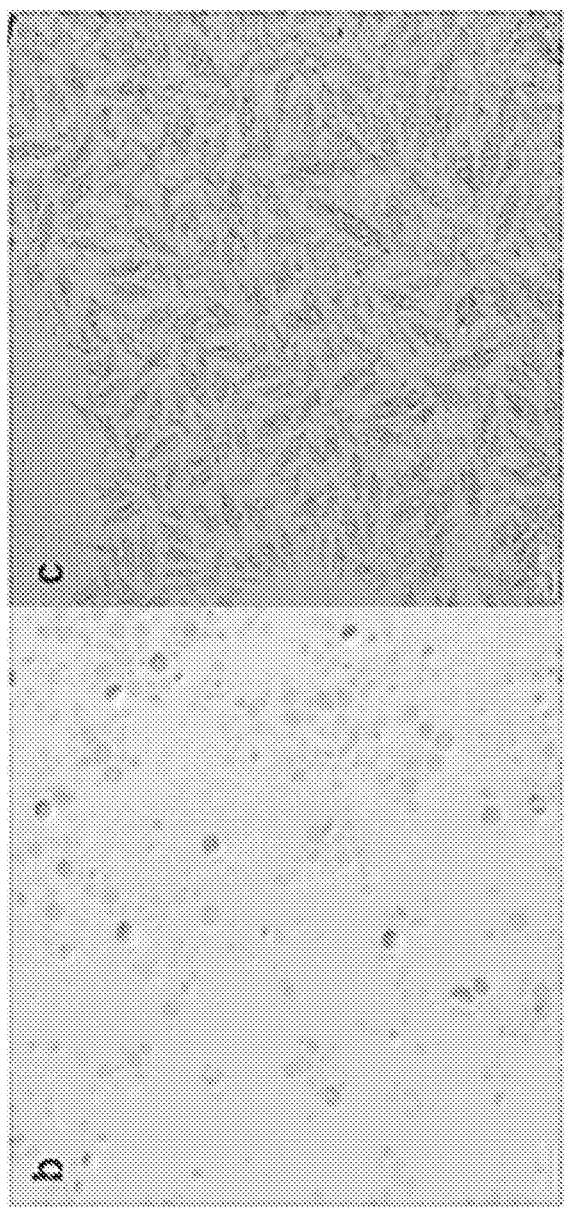

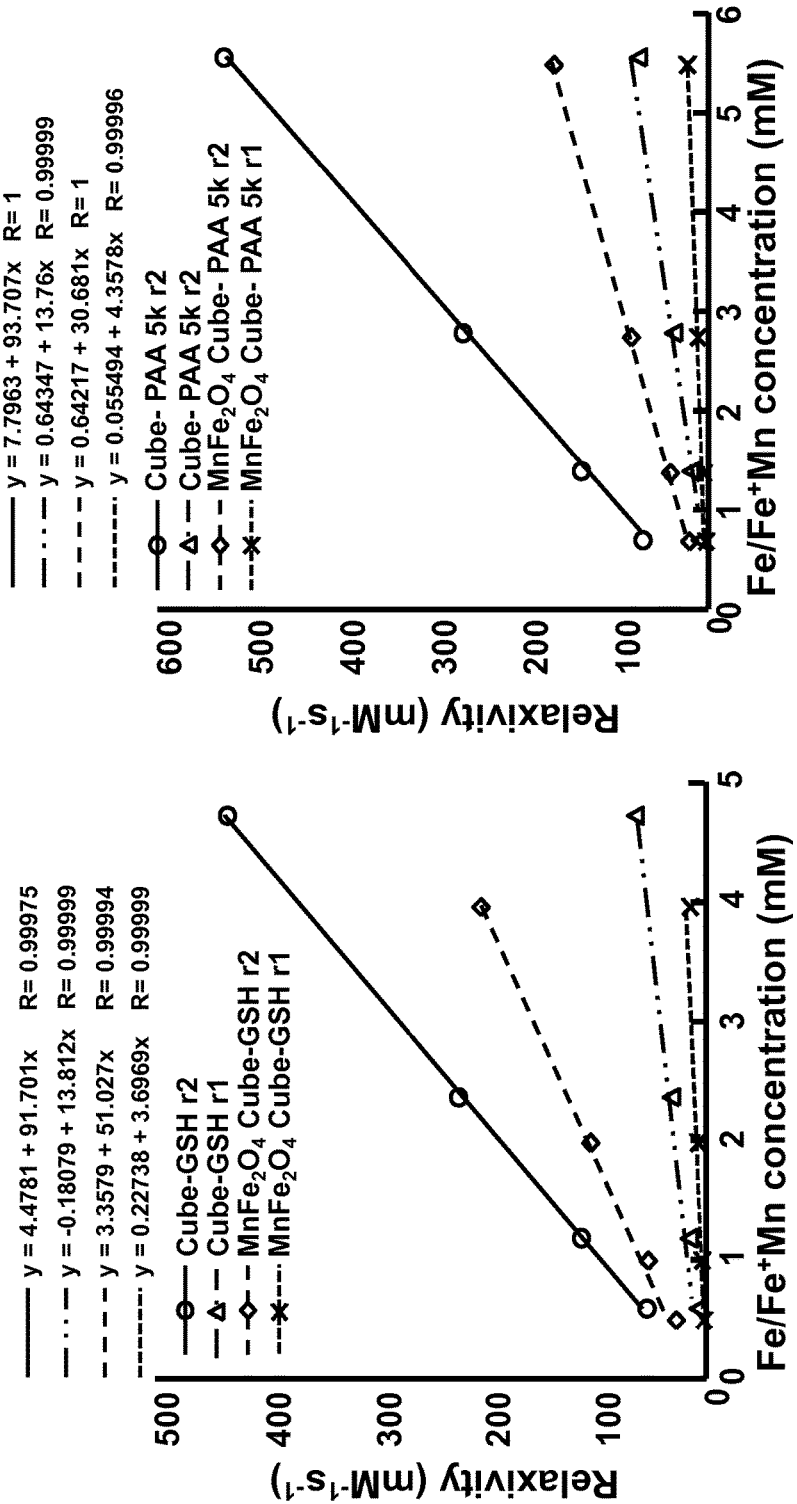

SHAPE-CONTROLLED MAGNETIC NANOPARTICLES AS T1 CONTRAST AGENTS FOR MAGNETIC RESONANCE IMAGING

CROSS-REFERENCE TO RELATED APPLICATIONS

This application claims priority to U.S. Provisional Patent Application Ser. No. 61/387,639, entitled "SHAPE-CONTROLLED MAGNETIC NANOSTRUCTURES AND METHODS OF SYNTHESIS, CONTRAST AGENTS, AND METHODS OF USE" filed on Sep. 29, 2010, and is a national phase application of and claims priority to PCT Application Serial No. PCT/US2011/053268 filed Sep. 26, 2011.

STATEMENT REGARDING FEDERALLY SPONSORED RESEARCH OR DEVELOPMENT

This invention was made with government support under award 907204 awarded by the National Science Foundation. The government has certain rights in the invention.

TECHNICAL FIELD

The present disclosure is generally related to ultrathin nanostructures, and to methods of making thereof using selected temperatures to control the dimensions of said nanostructures.

BACKGROUND

MRI is a powerful, non-invasive diagnostic tool for living organisms and provides real-time images with great spatial resolution (Terreno et al., (2010) *Chemical Reviews* 110: 3019-3042). The image contrast is based on the excitation and relaxation of water and lipids in tissues. The intrinsic longitudinal ($T_1$) and transverse ($T_2$) relaxation time of different parts of the tissues generate image contrast based on the MR signal intensity. Because of the small intrinsic variations in $T_1$ and $T_2$ of most tissues, contrast agents are routinely applied to enhance contrast by shortening the relaxation time of the protons in the neighboring water molecules (Strijkers et al., (2007) *Anti-cancer Agents in Medical Chemistry* 7; Waters et al., (2008) *Basic Res. Cardiol.* 103: 114-121; Yoo & Pagel (2008) *Frontiers in Bioscience* 13: 1733-1752; Na et al., (2009) *Advanced Materials* 21: 2133-2148). $T_1$ positive contrast agents mainly shorten the relaxation time $T_1$, generating a brighter image, while $T_2$ contrast agents produce a darker image by shortening the transverse relaxation time, $T_2$.

The effectiveness of a contrast agent is usually evaluated by its relaxivity $r_1$ or $r_2$, given by: $1/T_{isample}=1/T_{isolvent}+r_i[M]$ (i=1, 2). In this equation, $1/T_{isample}$ and $1/T_{isolvent}$ are the relaxation rates of the sample and pure solvent in $s^{-1}$, respectively, and [M] is the concentration of the contrast agent in mM. The ratio between $r_2$ and $r_1$ ($r_2/r_1$) is generally used to determine whether a contrast agent is suitable for $T_1$ or $T_2$ contrast (Strijkers et al., (2007) *Anti-cancer Agents in Medical Chemistry* 7). Normally, $T_1$ contrast agents have a lower ($r_2/r_1$) ratio (e.g., 1-2) while $T_2$ contrast agents have a larger ($r_2/r_1$) ratio (>10) (Tromsdorf et al., (2009) *Nano Letts.* 9: 4434-4440). $T_1$ positive contrast agents are clinically preferred because the brighter contrast brings higher resolution and is more easily detected in the MR images (Okuhata et al., (1999) *Advanced Drug Delivery Reviews* 37: 121-137).

$T_1$ contrast agents are generally paramagnetic $Gd^{3+}$ or $Mn^{2+}$ complexes (Caravan et al., (1999) *Chemical Reviews* 99: 2293-2352; Federle et al., (2000) *J. Magnetic Resonance Imaging* 12: 689-701). Their small sizes allow them to freely diffuse into extravascular space with low specificity (Caravan, P (2006) *Chem. Soc. Revs* 35: 512-523). Conjugation to macromolecules, such as dendrimers, (Cheng et al., (20090 *Adv. Functional Materials* 19: 3753-3759; Swanson et al., (2008) *Int. J. Nanomed.* 3: 201-210), liposomes (Ghaghada et al., (2008) *Academic Radiol.* 15: 1259-1263; Fossheim et al., (1999) *Magnetic Resonance Imaging* 17: 83-89; Zhang et al., (2009) *Europ. J. Radiol.* 70: 180-189), or proteins (Caravan, P. (2009) *Accounts of Chemical Res.* 42: 851-862; Yang et al., (2008) *J. Am. Chem. Soc.* 2008, 130: 9260-9267) has been explored to enhance the relaxivity and minimize the diffusion. Recently, $MnO^{18}$ and $Gd_2O_3$ (Park et al., (2009) *Acs Nano* 3: 3663-3669) nanoparticless have been developed as $T_1$ contrast agents (Na & Hyeon (2009) *J. Mat. Chem.* 19: 6267-6273). Unfortunately, the relaxivity of MnO nanoparticles is very low and $Gd^{3+}$-containing agents pose a long-term toxicity risk (Hasebroock & Serkova (2009) *Expert Opinion Drug Metab. Toxicol.* 5: 403-416). Continuing efforts are still needed to identify safer $T_1$ contrast agents. (Terreno et al., (2010) *Chemical Reviews* 110: 3019-3042; Schwert et al., (2002) *Contrast Agents I* 221: 165-199).

Superparamagnetic iron oxide nanoparticles (NPs) have been the primary choice for T2 contrast agents (Chu, G., (1994) *J. Biol. Chem.* 269: 787-790). They are generally believed to be safe and can be potentially reabsorbed through normal iron metabolic pathways (Weissleder et al., (1989) *Am. J. Roentgenol.* 152: 167-173; Stark et al., (1988) *Radiol.* 168: 297-301). Several types of iron oxide NPs have been developed for imaging liver, spleen, vascular compartments, and lymph nodes (Corot et al., (2006) *Adv. Drug Delivery Revs.* 58: 1471-1504) including clinically-approved FERIDEX™ ((2006) *Drug News & Perspectives* 7: 422-422) and RESOVIST™ (Reimer et al., (2003) *European Radiol.* 13: 1266-1276).

Because of the safer nature of iron oxide NPs and their intrinsic ma§netism, there has been initial interest in exploring their potential as $T_1$ contrast agents (Tromsdorf et al., (2009) *Nano Letts.* 9: 4434-4440; Federle et al., (2000) *J. Magnetic Resonance Imaging* 12: 689-701; Taboada et al., (2007) *Langmuir* 23: 4583-4588). The reported strategy was to decrease the size of iron oxide NPs to less than 5 nm. The s/v ratio of a spherical NP scales with 3/radius (e.g., 1.5 $nm^{-1}$ for a 4 nm NP and 0.5 $nm^{-1}$ for a 12 nm NP) and the fraction of surface atoms increases significantly (e.g., 40% for a 4 nm NP), as the NP size decreases. The surface atoms of NPs are normally coordinated by capping ligands. The complexation between the capping ligands and surface atoms forms a paramagnetic layer, which results in mixed paramagnetic and superparamagnetic behaviors in small NPs (Guardia et al., (2007) *J. Magnetism Magnetic Mats* 316: E756-E759). These small sized NPs show a much lower magnetization, and consequently decreased effects on the $T_2$ relaxation. Examples include 4 nm iron oxide NPs with a $r_2/r_1$ ratio as low as 2.4 at 1.4 Tesla (T) (Tromsdorf et al., (2009) *Nano Letts.* 9: 4434-4440), 1.3 nm ultra-small iron oxide NPs with a 1.6 $r_2/r_1$ ratio at 5 T, and 5 nm $Fe_2O_3$-citrate solution with a $r_2/r_1$ ratio of 2.46 at 20 MHz (Taboada et al., (2007) *Langmuir* 23: 4583-4588; Cho et al., (2006) *Nanotechnology* 17: 640-644). These lower $r_2/r_1$ ratios suggest that these NPs can be potentially used as $T_1$ contrast agents. However, when the NP size gets too small, the aggregation issue becomes critical (Tromsdorf et al., (2009) *Nano Letts.* 9: 4434-4440). In addition, small NPs (<8 nm) tend to experience fast renal clearance and escape from blood circulation (Longmire et al., (2008) *Nanomedicine* 3: 703-717). Therefore, it is important to examine other characteristics, such as surface coatings (LaConte et al., (2007) *J. Magnetic Resonance Imaging* 26: 1634-1641; Qin et al., (2007) *Advanced Materials* 19: 1874) and shapes (Joshi et al., (2009) *J. Physical Chem.* 113: 17761-17767; Park et al., (2008) *Advanced Materials* 20: 1630) which also affect the magnetic properties and T2 relaxation.

Anisotropic nanostructures have attracted much attention in various applications because of their unique electronic, magnetic, and optical properties (Cohen-Karni et al., (2010) *Nano Lett.* 10: 1098-1102; Chen et al., (2007) *Langmuir* 23: 4120-4129;). In particular, the synthesis of one-dimensional (1D) metallic and semiconductor nanostructures has been well documented (Baker et al., (2010) *Nano Lett.* 10: 195-201; Xia et al., (2009) *Angew. Chem. Int. Ed.* 48: 60-103; Lee et al., (2007) *J. Am. Chem. Soc.* 129: 10634-10635). Most recently, ultrathin (approximately 2 nm) nanowires (Cademartiri & Ozin (2009) *Adv. Mater.* 21: 1013-1020), such as Au (Li et al., (2008) *Nano Lett.* 8: 3052-3055; Wang & Sun (2009) *Chem.-an Asian J.* 4, 1028-1034; Poudyal et al., (2008) *Nanotechnology* 19: 355601-1-4; Huo et al., (2008) *Nano Lett.* 8: 2041-2044), FePt (Chen et al., (2007) *J. Am. Chem. Soc.* 129: 6348-6349), and oxides (Huo et al., (2009) *Nano Lett.* 9, 1260-1264; Yu et al., (2006) *J. Am. Chem. Soc.* 128: 1786-1787), have attracted much interest. In contrast, only few studies of ultrathin iron oxide magnetic nanoparticles have been reported (e.g., iron oxide nanobars and nanowires (Wang & Yang (2009) *Chem. Eng. J.* 147: 71-78). Spherical iron oxide nanoparticles have been primarily explored in targeted drug delivery, localized therapy, or as contrast agents for magnetic resonance imaging (MRI) (Pankhurst et al., (2003) *J. Phys. D-Appl. Phys.* 36: R167-R181; Veiseh et al., (2010) *Adv. Drug Deliv. Rev.* 62: 284-304). A recent study of ultrathin iron oxide nanoworms showed long blood circulation time, enhanced retention at tumor sites, and improved targeting efficiency (Park et al., (2008) *J. Adv. Mater.* 20: 1630-1635), which suggests that anisotropic iron oxide nanoparticles could potentially lead to further advancement in biomedical applications.

The synthetic approach to iron oxide spheres has been intensively focused on the thermal decomposition of iron (III) oleate complexes, due to its great reproducibility and control of the physical parameters (Park et al., (2004) *Nat. Mater.* 3: 891-895). In this method, the Fe(III) oleate precursor is typically heated up to over 300° C., producing different-sized spherical nanoparticles with a narrow size distribution. Cubic and bipyramid-shaped particles were also reported using this method as a result of the selective absorption of impurity ions, such as $Cl^-$, $Na^+$, or oleate (Shavel et al., (2007) *Adv. Funct. Mater.* 17: 3870-3876; Shavel et al., (2009) *Chem. Mater.* 21: 1326-1332; Shavel & Liz-Marzan (2009) *Phys. Chem. Chem. Phys.* 11: 3762-3766; Hai et al., (2010) *Colloid Interface Sci.* 346: 37-42; Kovalenko et al., (2007) *J. Am. Chem. Soc.* 129: 6352-6353; Xu et al., (2010) *Nanoscale* 2: 1027-1032; Kim et al., (2007) *J. Am. Chem. Soc.* 129: 5812-5813).

Even though the decomposition of the iron oleate complex is widely used for the synthesis of iron oxide nanoparticles, few mechanistic studies are available to understand the growth process. Hyeon (Kwon et al., (2007) *J. Am. Chem. Soc.* 129: 12571-12584) proposed that the dissociation of the first oleate ligand at around 200-240° C. triggered the nucleation event, followed by nanoparticle growth through the decomposition of the two remaining ligands above 300° C. However, it has been rather difficult to conclusively confirm the dissociation process of the iron oleate complex. A recent density functional theory (DFT) electronic structure calculation of iron carboxylate complexes showed different dissociation temperatures of the three carboxylate ligands (Lopez-Cruz & Lopez (2009) *Mol. Phys.* 107: 1799-1804. The first and the second ligands have similar dissociation temperatures, while the dissociation temperature of the third ligand was significantly higher. The calculations further proposed the formation of an Fe—O bond between the third ligand and the iron center. Unfortunately, an understanding of the chemical microenvironments of these three ligands and their effects on the nanostructure formation is still lacking.

SUMMARY

The disclosure encompasses embodiments of methods for synthesizing ultrathin nanostructures, the method comprising the steps of: (a) obtaining a metallic core-ligand complex precursor comprising a metallic moiety and a plurality of ligands attached to said metallic moiety; and (b) incubating the metallic core-ligand complex precursor mix at an incubation temperature selected from the group of: from about 100° C. to about 300° C., from about 100° C. to about 200° C., from about 100° C. to about 175° C., from about 100° C. to about 150° C., about 300° C., about 250° C., about 230° C., about 225° C., about 200° C., about 180° C., about 175° C., about 170° C., about 150° C., and about 125° C., wherein said temperature is selected to generate a population of ultrathin nanostructures by a process of thermal displacement of some or all of the ligand moieties from the metallic core.

In some embodiments of this aspect of the disclosure, the step of obtaining a metallic core-ligand complex precursor can comprise mixing a metallic core, at least one ligand species, and an organic solvent, thereby forming a metallic core-ligand complex precursor:organic solvent mix.

In some embodiments of this aspect of the disclosure, the ultrathin nanostructures can have at least one dimension of about 1 nm to about 4 nm.

In some embodiments of this aspect of the disclosure, the ultrathin nanostructures can have at least one dimension of about 2 nm.

In embodiments of this aspect of the disclosure, the metallic core can be a magnetic ferrite-based moiety selected from ferric oxide, ferrous oxide, a ferric ion, a ferrous ion, a manganese ferrite, a zinc ferrite, a copper ferrite, a chrome ferrite, a cobalt ferrite, a nickel ferrite, a non-ferrous metallic ion, and any combination thereof.

In some embodiments of this aspect of the disclosure, the plurality of ligands attached to the metallic core-ligand complex can comprise at least one fatty acid species, at least one non-fatty acid species, or at least one fatty acid species combined with at least one non-fatty acid species In embodiments of this aspect of the disclosure, the at least one fatty acid species can be a long-chain saturated fatty acid, a long-chain mono-unsaturated fatty acid, and a long-chain unsaturated fatty acid.

In some embodiments of this aspect of the disclosure, the at least one fatty acid species can be myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, myristic acid, palmitic acid, stearic acid, arachidic acid, behenic acid, lignoceric acid, cerotic acid, eicosenoic acid, mead acid, and nervonic acid.

In some embodiments of this aspect of the disclosure, the at least one fatty acid is oleic acid.

In some embodiments of this aspect of the disclosure, the at least one non-fatty acid ligand can be oleic acid, tri-N-octylphosphine oxide (TOPO), oleylamine, a Good's buffer, biotin, dopamine, histamine, a liquid crystal molecule, or any combination thereof.

In some embodiments of this aspect of the disclosure, the step of obtaining a metallic core-ligand complex precursor can comprise incubating a ferrite, a ferric salt, a ferrous salt, or a non-ferrous salt, with oleic acid or a salt thereof.

In some embodiments of this aspect of the disclosure, the incubation temperature can be selected to form a nanostructure structure selected from the group consisting of: a nanowhisker, a nanotube, a nanorice, a nanocube, and a nanosheet.

In one embodiments of this aspect of the disclosure, the metallic core-ligand complex can comprise ferric oxide complexed with a plurality of oleic acid moieties, and wherein said complex is incubated in the organic solvent at about 150° C., thereby forming a population of nanowhiskers.

Another aspect of the disclosure encompasses embodiments of a nanostructure synthesized according to the methods of the disclosure.

Another aspect of the disclosure encompasses embodiments of a pharmaceutically acceptable composition comprising a nanostructure synthesized according to the methods of the disclosure and a pharmaceutically acceptable carrier.

In some embodiments of this aspect of the disclosure, the pharmaceutically acceptable composition formulated to provide a high-contrast magnetic resonance image of a recipient animal or human subject.

Still another aspect of the disclosure encompasses embodiments of an ultrathin nanostructure that comprises a metallic core, the ultrathin nanostructure having at least one dimension of about 1 nm to about 4 nm and a substantially reduced relaxivity compared to a nanostructure having dimensions of at least 4 nm.

In some embodiments of this aspect of the disclosure, the ultrathin nanostructure can have at least one dimension of about 2 nm or less.

In some embodiments of this aspect of the disclosure, the metallic core can be a magnetic ferrite-based moiety selected from the group consisting of: a ferric oxide, a ferrous oxide, a ferric ion, a ferrous ion, a manganese ferrite, a zinc ferrite, a copper ferrite, a chrome ferrite, a cobalt ferrite, and a nickel ferrite.

In some embodiments of this aspect of the disclosure, the ultrathin nanostructure can be a nanowhisker, a nanotube, a nanorice, a nanocube, or a nanosheet.

In some embodiments of this aspect of the disclosure, the ultrathin nanostructure can further comprise a biocompatible coating.

In some embodiments of this aspect of the disclosure, the ultrathin nanostructure can further comprise a targeting ligand disposed on the surface of the ultrathin nanoparticle.

In some embodiments of this aspect of the disclosure, the ultrathin nanostructure can further comprise at least one of the group consisting of: polyacrylic acid (PAA), polyethyleneimine (PEI), glutathione (GSH), lactobionic acid (LBA), histamine, dopamine, L-DOPA, and biotin disposed on the ultrathin nanostructure.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1A illustrates the conversion of Fe(III)-oleate to nanowhiskers by heating to about 150° C.

FIG. 2A is a graphical TGA plot of a Fe(III) oleate complex at a heating rate of 1° C./min.

FIG. 2B is a graph illustrating a isothermal analysis of a Fe(III) oleate complex at 150° C.

FIG. 4A is a series of digital images showing time-dependent morphology evolution of nanowhiskers: at (Panel a) 0.5 h; (Panel b) 6 h: (Panel c) 22 h.

FIG. 4B illustrates a M-H curve of assembled nanowhisker bundles.

FIG. 6A illustrates the optimized structures of the Fe(II) oleate complex.

FIG. 6B is a digital image of irregular particles from decomposition of Fe(II) oleate.

FIG. 6C is a digital image of a mixture of sphere-like nanoparticles and nanowhiskers from the decomposition of the Fe(II) and Fe(III) oleate complex mixture.

FIG. 7A illustrates the relaxed structure of $Fe_{39}O_{62}(HCOO)_{12}$.

FIG. 7B illustrates the structure of a simulated iron oxide nanocluster structure with oleate ligand shell.

FIG. 7C is a graph illustrating TGA plot of iron oxide nanowhiskers.

FIG. 9A is a digital image showing a TEM image of intermediate samples at reaction time of 1 hour.

FIG. 9B is a digital image showing a TEM image of intermediate samples at reaction time of 1.5 hours.

FIG. 10A is a digital image of a temperature-dependent nanostructural morphology-paste-like, 100° C.

FIG. 10B is a digital image of a temperature-dependent nanostructural morphology-nanowhiskers, 180° C.

FIG. 10C is a digital image of a temperature-dependent nanostructural morphology-irregular nanoparticles, 230° C.

FIG. 10D is a digital image of a temperature-dependent nanostructural morphology-nanoparticles, 320° C.

FIG. 11A is a graph illustrating a TGA plot of Fe(II) and Fe(II)/Fe(III) oleate complex mixtures.

FIG. 12B is a digital image illustrating iron oxide nanowhiskers synthesized with OA and ON.

FIG. 13B is a digital image of a sample produced using Fe(II) stearate at 230° C.

FIG. 13C is a digital image of a sample produced using Fe(III) stearate at 230° C.

FIG. 16A is a graph illustrating doping-dependent relaxivities of glutathione (GSH)-coated iron oxide nanocubes and $MnFe_2O_4$ nanocubes.

FIG. 16B is a graph illustrating doping-dependent relaxivities of PAA (5 kD)-coated iron oxide nanocubes and $MnFe_2O_4$ nanocubes.

Figures 1B, 1C:
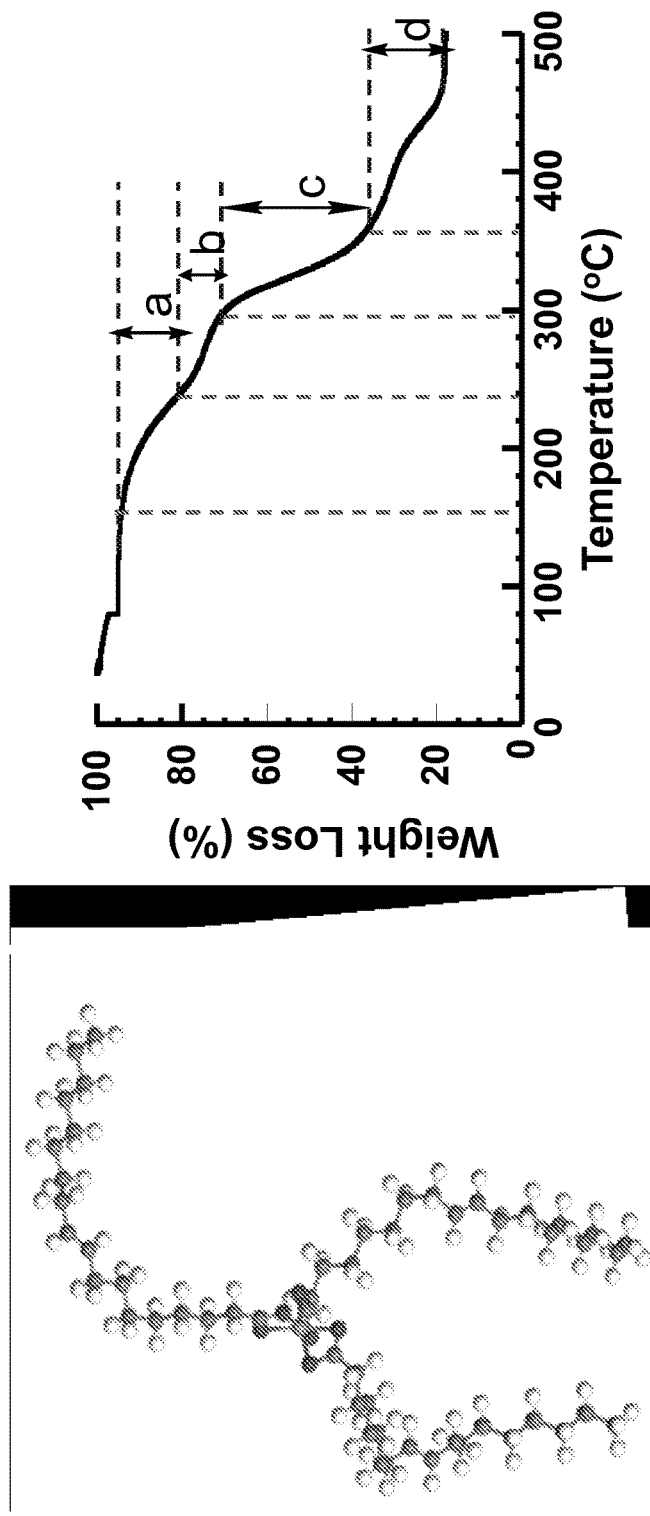
FIG. 1B illustrates an optimized structure of the iron oleate complex based on DFT calculations.
FIG. 1C is a graph illustrating a TGA plot for the iron oleate complex.

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

ABBREVIATIONS tri-octylphosphine oxide, TOPO; thermogravimetric analysis, (TGA; oleyamine, ON; oleic acid, OA; polyacrylic acid, PAA; polyethyleneimine, PEI; glutathione, GSH; lactobionic acid, LBA.

DEFINITIONS

The term "ultrathin magnetic nanostructure" as used herein refers to a nanostructure wherein at least one dimension thereof is about 4 nm or less, or of about 2 nm or less. Typically, nanoparticles are understood to include particles of a size (e.g., diameter for spherical or substantially spherical nanoparticles, or the longest dimension of a non-spherical nanoparticle) of about 10 to 500 nm, about 10 to 250 nm, about 10 to 100, or about 10 nm to 50 nm. The nanoparticles manufactured by the method of the present disclosure are therefore smaller in at least one dimension than any of the dimensions of the generally known nanoparticles. For example, a nanowhisker is a structure having a diameter of about 2 nm and a length of between about 10 to about 30 nm. One embodiment, for example, has the dimensions of about 2 nm and a length of between about 20 nm. It is contemplated that the ultrathin nanostructures of the disclosure may have any form including, but not limited to, a nanowhisker, a nanocube, a nanofiber, a nanosheet, and the like.

The term "metallic core-ligand complex precursor" as used herein refers to a structure comprising at its core a metallic moiety. The metallic moiety can be, but is not limited to, a ferrite moiety a ferric ion, and having attached thereto by coordination bonds at least one, and preferably a plurality of, fatty acid or non-fatty acid ligand moieties, wherein in the plurality of ligand moieties can be at least one fatty acid species at least one non-fatty acid species, a plurality of fatty acid species, a plurality of non-fatty acid species, or a combination of different fatty acid and non-fatty acid species.

The terms "metallic core" and "metallic core" as used herein refer to a metal ion or combination of metal ions that may be ferrous, non-ferrous, or a combination of ferrous and non-ferrous metal ions. A magnetic moiety comprising a ferrite, a ferric or ferrous ion, and optionally further comprising a non-ferrous metal such as, but not limited to, zinc, copper, magnesium, manganese, and the like. It is further contemplated that the metallic core may further not include a ferric or ferrous ion but be any metal that may be detected by an MRI method, such as manganese or magnesium.

The term "ligand moiety" as used herein refers to a fatty acid such as, but not limited to, a long-chain fatty acid that can be, but not necessarily attached to a positively charged metallic core moiety by electrostatic attraction. It is contemplated that the ligands of the metallic core-ligand complex in this disclosure precursor can comprise a single fatty acid species, a mixture of fatty acid species, a single species of another non-fatty acid molecules, such as, but not limited to oleylamine, a Good's buffer (MES, ADA, PIPES, ACES, Cholamine chloride, BES, TES, HEPES, Acetamidoglycine, Tricine, Glycinamide, Bicine), biotin, dopamine, histamine, liquid crystal molecules, or a single fatty acid species or mixed population of fatty acids species in combination with at least one other non-fatty acid species ligand.

The term "incubation temperature" as used herein refers to the temperature at which a metallic core-ligand precursor may be heated to form nanostructures having at least one-dimension of about 2 nm or less according to the disclosure. In the methods of the disclosure, the incubation temperature may be in a range selected from the group of: from about 100° C. to about 300° C., from about 100° C. to about 200° C., from about 100° C. to about 175° C., from about 100° C. to about 150° C., about 300° C., about 250° C., about 230° C., about 225° C., about 200° C., about 180° C., about 175° C., about 170° C., about 150° C., and about 125° C.

The term "selected to generate" as used herein refers to an incubation temperature of less than about 300° C. that may be selected for the generation of a nanostructure detectable by MRI and which has at least one dimension of about 4 nm or less, and preferably of about 2 nm or less.

The term "thermal displacement" as used herein refers to the act of heating a ferrite-ligand complex precursor, in an organic solvent, whereby the ligands attached to the metallic core are removed therefrom by the application of heat. Under the conditions of the methods of the disclosure, it is contemplated that ligands may be progressively removed from a metallic core by increasing the applied heat or by extending the period of application of the heat. Removal of an oleate ligand from a ferric core by the methods of the disclosure at a temperature of less than 300° C., such as 150° C., allows for the removal of a single oleic acid moiety from each precursor, whereupon the remaining ferrite-ligand precursors may form the ultrathin (<2 nm) nanostructures of the disclosure.

The term "ferrite" as used herein refers to a mixed oxide with a general structure $AB_2O_4$ (A and B are two different metal ions) such as, but not limited to, magnetite ($F_3O_4$), maghemite ($Fe_2O_3$), a manganese ferrite, a zinc ferrite, a copper ferrite, a chrome ferrite, a cobalt ferrite, and a nickel ferrite The term "fatty acid, as used herein refers to a carboxylic acid with a long unbranched aliphatic tail that is either saturated or unsaturated. Most naturally occurring fatty acids have a chain of an even number of carbon atoms, from 4 to 28. When they are not attached to other molecules, they are known as "free" fatty acids. Unsaturated fatty acids have one or more double bonds between carbon atoms. Saturated fatty acids are long-chain carboxylic acids that usually have between 12 and 24 carbon atoms and have no double bonds. Thus, saturated fatty acids are saturated with hydrogen (since double bonds reduce the number of hydrogens on each carbon). Because saturated fatty acids have only single bonds, each carbon atom within the chain has two hydrogen atoms (except for the omega carbon at the end that has three hydrogens).

It is contemplated that the ligands of the metallic core-ligand complexes of the disclosure may be a single type of fatty acid, such as, but not limited to, oleic or stearic acids, of any of myristoleic acid, palmitoleic acid, sapienic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, myristic acid, palmitic acid, arachidic acid, behenic acid, lignoceric acid, cerotic acid, eicosenoic acid, mead acid, and nervonic acid. It is further contemplated that the ferrite-ligand complex precursor may include more than one fatty acid species attached to the underlying metallic core such as, but not limited to, two oleic acid chains and a stearic acid chain.

The terms "ferric salt" and "ferrous salt" as used herein refers to any small molecule salt such as, but not limited to, halide, nitrate, sulfate, and the like.

The term "Magnetic Resonance Imaging" or (MRI) as used herein is a method to obtain an image representing the chemical and physical microscopic properties of materials, by utilizing a quantum mechanical phenomenon, named Nuclear Magnetic Resonance (NMR), in which a system of spins, placed in a magnetic field resonantly absorb energy, when applied with a certain frequency.

A nucleus can experience NMR only if its nuclear spin I does not vanish, i.e., the nucleus has at least one unpaired nucleon. Examples of non-zero spin nuclei frequently used in MRI include $^1$H (I=1/2), $^2$H (I=1), $^{23}$Na (I=3/2), etc. When placed in a magnetic field, a nucleus having a spin I is allowed to be in a discrete set of energy levels, the number of which is determined by I, and the separation of which is determined by the gyromagnetic ratio of the nucleus and by the magnetic field. Under the influence of a small perturbation, manifested as a radiofrequency magnetic field, which rotates about the direction of a primary static magnetic field, the nucleus has a time dependent probability to experience a transition from one energy level to another. With a specific frequency of the rotating magnetic field, the transition probability may reach the value of unity. Hence at certain times, a transition is forced on the nucleus, even though the rotating magnetic field may be of small magnitude relative to the primary magnetic field. For an ensemble of spin I nuclei the transitions are realized through a change in the overall magnetization.

Once a change in the magnetization occurs, a system of spins tends to restore its magnetization longitudinal equilibrium value, by the thermodynamic principle of minimal energy. The time constant which control the elapsed time for the system to return to the equilibrium value is called "spin-lattice relaxation time" or "longitudinal relaxation time" and is denoted $T_1$. An additional time constant, $T_2$, called "spin-spin relaxation time" or "transverse relaxation time", controls the elapsed time in which the transverse magnetization diminishes, by the principle of maximal entropy. However, inter-molecule interactions and local variations in the value of the static magnetic field, alter the value of $T_2$, to an actual value denoted $T_2^*$.

In MRI, a static magnetic field having a predetermined gradient is applied on an object, thereby creating, at each region of the object, a unique magnetic field. By detecting the NMR signal, knowing the magnetic field gradient, the position of each region of the object can be imaged. In MRI, pulse sequences are applied to the object (e.g., a patient) to generate NMR signals and obtain information therefrom, which is subsequently used to reconstruct images of the object. The above mentioned relaxation times and the density distribution of the nuclear spin are properties which vary from one normal tissue to the next, and from one diseased tissue to the next. These quantities are therefore responsible for contrast between tissues in various imaging techniques, hence permitting image segmentation.

A common characteristic for all of these techniques is that the properties of water molecules are measured, which properties are indirectly dependent on interaction with macromolecules such as proteins.

Connective tissues, such as ligaments, tendons and cartilage appear in standard magnetic resonance (MR) images with low signal-to-noise (S/N) ratio (SNR) due to the water long $T_2$ relaxation times. Images performed with short echo time (TE), result in a significant loss of contrast. In addition to the need to enhance the NMR signal of connective tissues, it is also important to increase the contrast between the different compartments within a specific tissue and between adjacent tissues.

The term "pharmaceutically acceptable carrier" as used herein refers to a diluent, adjuvant, excipient, or vehicle with which a heterodimeric probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the heterodimeric probe and pharmaceutically acceptable carriers can be sterile. Water is a useful carrier when the heterodimeric probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The term "target" as used herein refers to a polypeptide for which it is desired to detect. The target polypeptide for use in the methods herein disclosed may be an isolated polypeptide, a polypeptide immobilized on a solid support or in free solution. Alternatively, the target polypeptide may be on a cell surface, the cell being isolated from an animal host, a cultured cell or a cell or population of cells in a tissue of an animal.

Nanoparticles of the disclosure comprise a "coat" of a second material that surrounds the core. A coat can include a layer of material, either organic or inorganic, that covers the surface of the core of a nanoparticle. A coat may be crystalline, polycrystalline, or amorphous and optionally comprises dopants or defects.

A coat may be "complete", indicating that the coat substantially or completely surrounds the outer surface of the core (e.g., substantially all surface atoms of the core are covered with coat material). Alternatively, the coat may be "incomplete" such that the coat partially surrounds the outer surface of the core (e.g., partial coverage of the surface core atoms is achieved). In addition, it is possible to create coats of a variety of thicknesses, which can be defined in terms of the number of "monolayers" of coat material that are bound to each core. A "monolayer" is a term known in the art referring to a single complete coating of a material (with no additional material added beyond complete coverage). For certain applications, coats will preferably be of a thickness between about 0 and about 10 monolayers, where it is understood that this range includes non-integer numbers of monolayers. Non-integer numbers of monolayers can correspond to the state in which incomplete monolayers exist. Incomplete monolayers may be either homogeneous or inhomogeneous, forming islands or clumps of coat material on the surface of the nanoparticle core. Coats may be either uniform or nonuniform in thickness. In the case of a coat having nonuniform thickness, it is possible to have an "incomplete coat" that contains more than one monolayer of coat material. A coat may optionally comprise multiple layers of a plurality of materials in an onion-like structure, such that each material acts as a coat for the next-most inner layer. Between each layer there is optionally an interface region. The term "coat" as used herein describes coats formed from substantially one material as well as a plurality of materials that can, for example, be arranged as multi-layer coats.

A nanoparticle of the disclosure may optionally comprise a "ligand layer" comprising one or more surface ligands (e.g., peptide that may specifically bind a target molecule on a cell) surrounding the core of the nanoparticle. A nanoparticle comprising a ligand layer may or may not also comprise a coat. As such, the surface ligands of the ligand layer may bind, either covalently or non-covalently, to either the core or the coat material or both (in the case of an incomplete coat). The ligand layer may comprise a single type of surface ligand (e.g., a single molecular species) or a mixture of two or more types of surface ligands (e.g., two or more different molecular species). A surface ligand can have an affinity for, or bind selectively to, the nanoparticle core, coat, or both at least at one point on the surface ligand. The surface ligand may optionally bind at multiple points along the surface ligand. The surface ligand may optionally contain one or more additional active groups that do not interact specifically with the surface of the quantum dot.

It will be understood by one of ordinary skill in the art that when referring to a population of nanoparticles as being of a particular "size", what is meant is that the population is made up of a distribution of sizes around the stated "size". Unless otherwise stated, the "size" used to describe a particular population of nanoparticles will be the mode of the size distribution (i.e., the peak size). By reference to the "size" of a nanoparticle is meant the length of the largest straight dimension of the nanoparticle. For example, the size of a perfectly spherical nanoparticle is its diameter.

DESCRIPTION

The present disclosure provides methods for the generation of nanostructures suitable for use in magnetic resonance imaging where the nanostructures have at least one dimension of about 2 nm or less. As indicated by their relaxivity properties, the ultrathin nanoparticles are suitable for providing high-contrast MRI images when delivered to a recipient animal or human subject. In particular, the methods of the disclosure comprise the selective use of incubation temperatures that result in the controlled removal of fatty acid ligands from metallic cores to which they are attached, allowing the metallic cores or the precursor moieties to unite to form nanostructures of defined and predictable shapes, but having at least one dimension significantly less that at least one other dimension. Accordingly, the nanostructures of the disclosure may be ultrathin sheets, rods, whiskers and the like, or even structures that are thin and porous resembling rice grains. Unlike known procedures for forming nanoparticles, the temperatures useful in the methods of the disclosure are less than 300° C. and allow for progressive elevation of the incubation temperature.

The methods of the disclosure are especially advantageous for synthesizing nanoparticles that may be administered to an animal or human subject for providing high-contrast imaging with magnetic resonance. Accordingly, the nanostructures of the disclosure comprise a metallic core, most typically, but not necessarily limited to, a ferrite moiety that can be a ferrous or ferric ion alone or in combination with other metallic elements. However, it is contemplated that the methods of the disclosure are also suitable for generating nanostructures with non-ferrous cores such as magnesium or manganese cores.

It is further contemplated that the ultrathin nanostructures of the disclosure may further comprise a targeting ligand suitable for concentrating the particles at a selected target site in a recipient animal or human subject, including, but not limited to, a receptor ligand, a target-specific antibody or a fragment thereof, and the like. It is also contemplated that the ultrathin nanostructures of the disclosure may further comprise at least one biocompatible coating such as, but not limited to, a polyethylene glycol, a polysaccharide, a synthetic polymer, and the like to improve the half-life or clearance of the structures in a subject, or to which may be attached one or more of the targeting ligands.

DFT calculations of the Fe(III) oleate complex predict a large difference among the binding energies of the three ligands. Experimentally, such a difference was reflected by the distinct weight losses of the thermogravimetric analysis (TGA) plot of the Fe(III) oleate complex. The different bindings allowed the selective decomposition of the more weakly-bound ligands at 150° C., forming iron oxide nanoclusters through ligand-directed growth. The methods of the present disclosure provide shape-controlled iron oxide nanoparticles, which demonstrates the importance of the chemical microenvironments and offers insight into nanoparticle synthesis mechanisms.

Synthesis of iron oxide nanowhiskers according to the methods of the disclosure starts with the preparation of an iron oleate complex followed by selective decomposition at 150° C. The ligand coordination environments of the Fe(III) oleate complex were investigated using DFT electronic structure calculations and TGA measurements. FIG. 1B shows an optimized geometric structure of the Fe(III) oleate complex obtained from electronic structure calculations. FIG. 1A schematically illustrates the conversion of such a complex to nanowhiskers by a method of the disclosure. This complex has a $FeO_6$ quasi-octahedral core structure with a non-equivalent arrangement of three ligands: two symmetric bonds and one asymmetric bond. The calculated binding energies of two of those ligands are very similar (7.0 and 10.5 eV) but the binding energy of the third one is much higher (39.2 eV). The lower binding energies are likely associated with the two symmetric ligands with a weak binding to the Fe(III) center. These calculated binding energies agree with previously-reported simulations of Fe(III) carboxylate complexes, which showed two ligands with low dissociation temperatures and one with a much higher dissociation temperature (Lopez-Cruz & Lopez (2009) *Mol. Phys.* 107: 1799-1804).

The thermal decomposition behavior of the Fe(III) oleate complex was experimentally studied using TGA measurements, which provide an indirect prediction of the ligand binding strength of the complex. Accordingly, FIG. 1C illustrates a TGA plot obtained at a constant heating rate of 5° C./min. The initial weight loss before 100° C. was due to the evaporation of the adsorbed solvents from the synthesis of the iron oleate complex. The second distinct weight loss started at about 150° C. and continued until about 230° C. (as shown in FIG. 1C, region a), and this loss was attributed to the dissociation of the two symmetric ligands with lower binding energies. The small percentage weight loss in the range of about 230° C. to about 295° C. was from the decomposition of the third ligand (see FIG. 1C, region b). During these two steps of ligand decomposition, the weight losses were mainly from the release of $CO_2$ gas with a decomposition ratio close to 2:1. The decomposition ratio agrees very well with DFT calculations that two of the ligands have lower binding energies. The chemical reaction associated with this process can be reasonably explained using the ketonic decarboxylation reaction:

(equation 1)

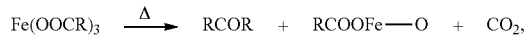

$$Fe(OOCR)_3 \xrightarrow{\Delta} RCOR + RCOOFe\text{—}O + CO_2, \quad (1)$$

as suggested in heating studies of iron carboxylate (Garg & Lanjewar (1995) *J. Radioanaly. Nucl. Chem. Lett.* 199: 443-452; Davis & Schltz (1962) *J. Org. Chem.* 27: 854-857; Ganguly et al., (2008) *J. Chem. Sci.* 120: 521-528). The detailed reaction process is believed to occur through the decomposition and recombination of several radical species (e.g., RCOO* and RC*O). The continuous weight loss between about 295° C. and about 345° C. can be attributed to desorption of the decomposed ligands (as shown in FIG. 1C, region c). Finally, vaporization of all organic compounds resulted in further weight losses above about 350° C. (as shown in FIG. 1C, region d).

To obtain further insight into the weight loss at 150° C., TGA analysis at a slower heating rate (1° C./min) and an isothermal analysis at 150° C. for 3.5 hours were performed (as shown in FIGS. 2A and 2B, respectively). The TGA plot at a slower heating rate (FIG. 2A) demonstrated the same weight loss onset at around 150° C., but it continued until 200° C., suggesting a slow decomposition process of the two symmetric ligands. The isothermal analysis performed at 150° C. (as shown in FIG. 2B) reached a weight loss of 9% after approximately 2.5 hours, also indicating a slow dissociation process of the two symmetric ligands while heating. The weight loss was primarily due to the release of $CO_2$ gas from the ketonic decarboxylation reaction. The isothermal TGA analysis also indicates the high stability of the third ligand at 150° C., where continuous weight loss was not observed.

The DFT calculations and TGA measurements of the present disclosure indicate a difference in the ligand coordination environments within a Fe(III) oleate complex. A synthesis, therefore, was performed to selectively decompose the more weakly-bound ligands at 150° C. to allow nanoparticle formation, contrary to previous indicators (Park et al., (2004) *Nat. Mater.* 3: 891-895; Xu et al., (2010) *Nanoscale* 2: 1027-1032; Roca et al., (2006) *J. IEEE Trans. Magn.* 42: 3025-3029).

Figure 3B:
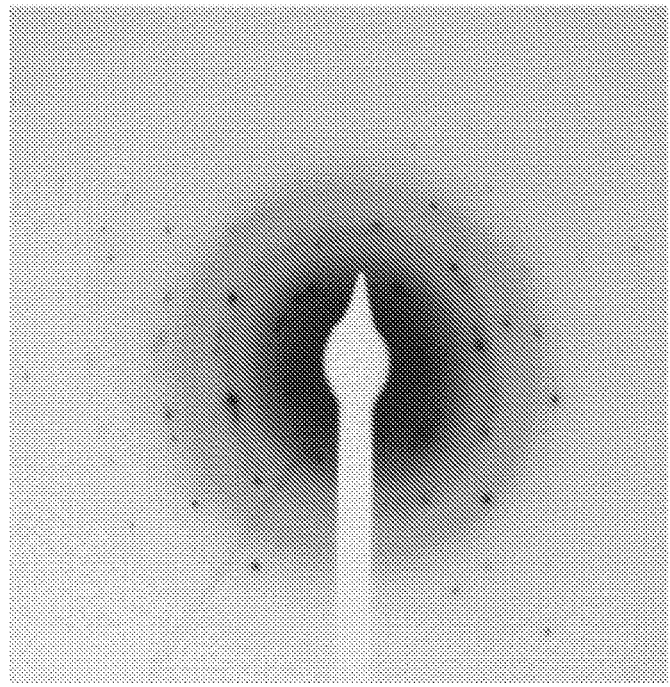
FIG. 3B is a digital image of an electron diffraction pattern of iron-oxide whiskers.
Figure 3A:
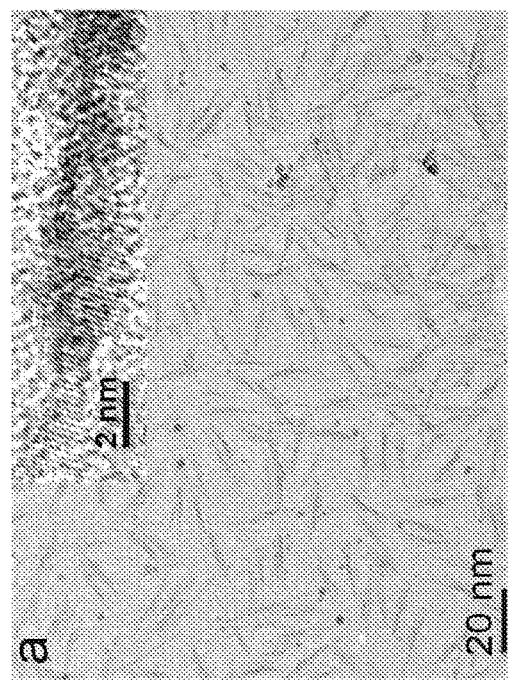
FIG. 3A is a digital bright-field TEM image, and an HRTEM image (insert) of iron-oxide whiskers.
Figure 3C:
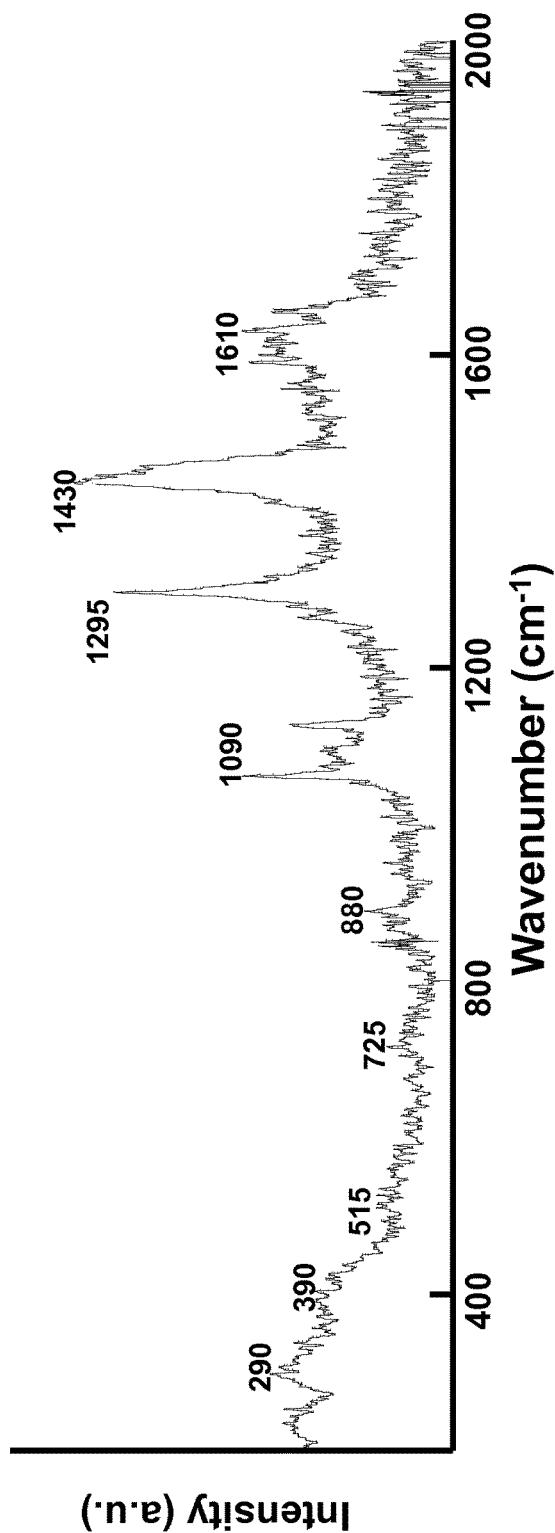
FIG. 3C illustrates a Raman spectrum of iron-oxide whiskers.
Figure 8:
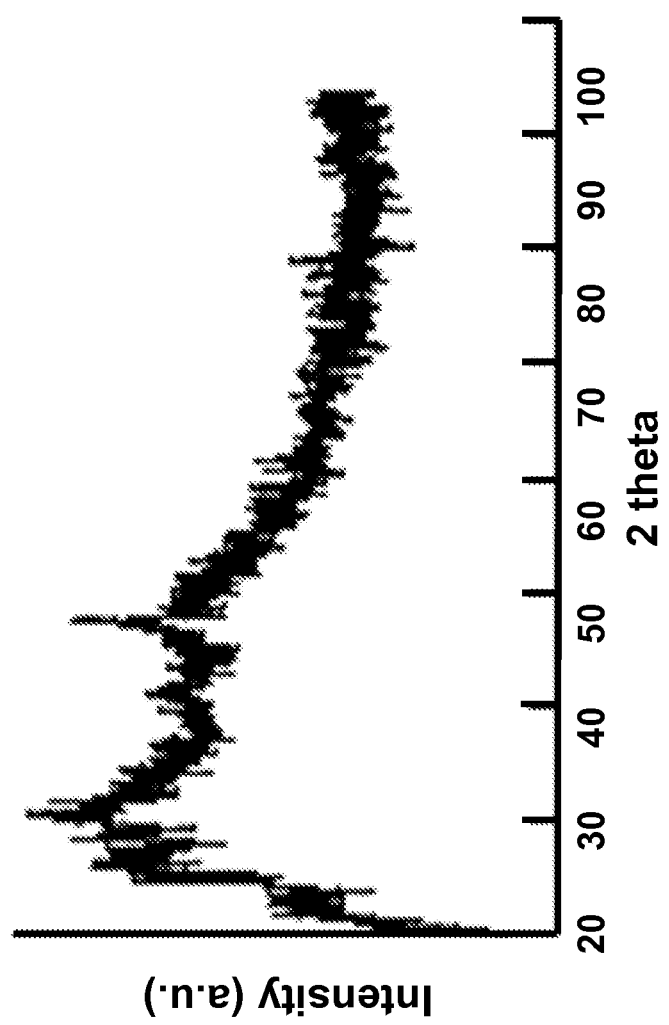
FIG. 8 illustrates an X-ray diffraction (XRD) scan of iron oxide nanowhiskers according to the disclosure.

Iron oxide nanowhiskers with dimensions of approximately 2×20 nm were formed after 2.5 hours of heating, as shown in FIG. 3A. A high resolution TEM image of a single nanowhisker showed clear lattice fringes, indicating the crystallinity of these nanostructures is shown in (FIG. 3A, inset). The calculated interfringe distance of 0.298 nm was close to the interfringe distance of the {220} plane of the cubic iron oxide spinel structure. The electron diffraction pattern collected on several nanowhiskers agreed well with the $Fe_2O_3$ crystal phase, as shown in FIG. 3B. The observed diffraction dots rather than rings also indicated the crystallinity of these nanowhiskers. However, the x-ray diffraction scan did not allow confirmation their crystal phases, due to the significant size broadening, as shown in FIG. 8.

To further confirm the crystal phase, a Raman spectrum of these nanowhiskers was collected using a Bruker Senterra system, as shown in FIG. 2C. The absence of the major feature peak of $Fe_3O_4$ at around 670 $cm^{-1}$ indicated that these nanowhiskers were not magnetite phase (Kwon et al., (2006) *Chem. Mater.* 18: 6357-6363); in contrast, the main peaks of 725, 1295, 1430 $cm^{-1}$ can be assigned to the $\gamma$-$Fe_2O_3$ phase (Park et al., (2010) *Nanotechnology* 21: 225708-1-8). While not wishing to be bound by any one theory, these iron oxide nanostructures are unlikely in the $\alpha$-$Fe_2O_3$ phase, because the Raman peaks for $\alpha$-$Fe_2O_3$ would be much shaper, especially in the region of 200-400 $cm^{-1}$ phase (Kwon et al., (2006) *Chem. Mater.* 18: 6357-6363). The broad peak around 1610 $cm^{-1}$ corresponded to adsorbed moisture or —OH groups.

Figures 3D, 3E:
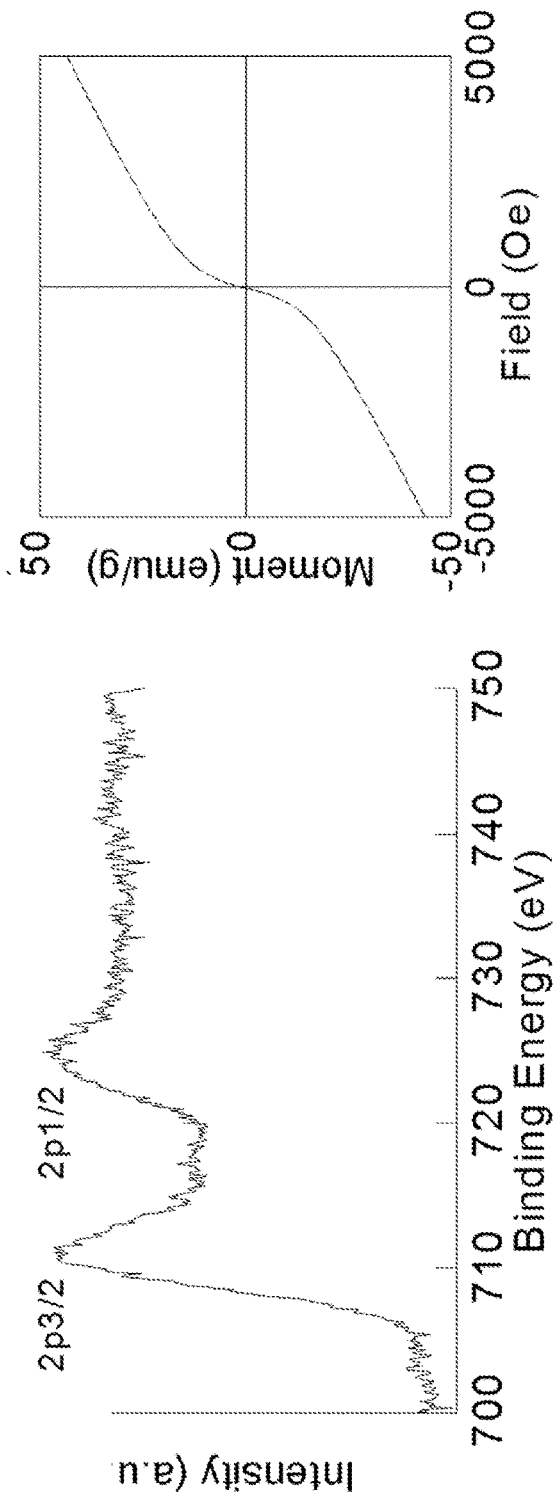
FIG. 3D illustrates an Fe2p core-level spectrum of iron-oxide whiskers.
FIG. 3E illustrates a room temperature M-H curve of iron-oxide whiskers.

Additionally, XPS analysis was performed to confirm the Fe valence states of the nanowhiskers. This technique has been utilized as an effective tool for differentiating magnetite ($Fe_3O_4$) from maghemite ($\gamma$-$Fe_2O_3$). FIG. 3D illustrates the core-level XPS pattern of the nanowhiskers in the Fe2p region. The two major peaks at 710.7 and 725.0 eV corresponded to the $2p_{3/2}$ and $2p_{1/2}$ core levels of iron oxide. Small satellite signals around 718.0, 730.0, and 745.0 eV were an indicator of $\gamma$-$Fe_2O_3$ rather than $Fe_3O_4$.

The magnetization versus applied field (M-H) curve of these nanowhiskers showed mixed superparamagnetic and paramagnetic signals, without saturation, as shown in FIG. 3E. The observed magnetic property results from the high surface to volume ratio and surface iron-ligand complexation. Compared to spherical or cubic shaped nanoparticles, the thin nanowhiskers of the present disclosure have much higher surface to volume ratios. Further, the high percentage of surface atoms was linked to oleate ligands through coordination bonds, behaving as iron complexes. The surface effects generate a magnetic "dead layer" on the nanoparticle surfaces, observed in other small magnetic nanoparticle systems (Guardia et al., (2007) *J. Magn. Magn. Mater.* 316, E756-E759; Kachkachi et al., (2000) *Eur. Phys. J. B* 14: 681-689; Koseoglu et al., (2006) *Phys. Status Solidi A* 203: 1595-1601; Millan et al., (2007) *J. Magn. Magn. Mater.* 312: L5-L9; Koseoglu & Kavas (2008) *J. Nanoscience and Nanotechnology* 8: 584-590). Theoretical simulations also indicated that the dead layer is around 1 nm thick, and this effect could be significant in high surface to volume ratio nanostructures, as observed in our nanowhisker system.

The growth process of the nanowhiskers was monitored by taking samples out of the reaction solution at different time intervals. These intermediate solutions were directly deposited on TEM grids without any wash or other treatments to capture the intermediate nanostructural morphologies, as shown in FIG. 4A, panels a-c. At 0.5 hrs, structures with no clear morphology on a dark background were observed (FIG. 4A, panel a), and the nanowhiskers were not produced. As time progresses, the paste morphology started to break down, forming structures with ultrathin morphology at 1 hr, as shown in (FIG. 9A). At a reaction time of 1.5 hrs, many nanowhiskers could be clearly observed (FIG. 9B). After 2.5 hrs (the normal reaction time), iron oxide nanowhiskers were the primary product, as seen in FIG. 3A. The whisker morphology remained after 6 hrs of heating (FIG. 4A, panel b). However, continuous heating (to about 22 h) led to the formation of assembled nanowhisker bundles or sheets, as shown in FIG. 4A, panel c)). Compared to the mixed paramagnetic and ferromagnetic signals of the isolated nanowhiskers, the nanowhisker bundles were ferromagnetic, as indicated by the open loop in the M-H curve shown in FIG. 4B. But, the whisker morphology can still be clearly identified within the bundles, an indication of the nanowhisker stability at the reaction temperature.

Figure 5:
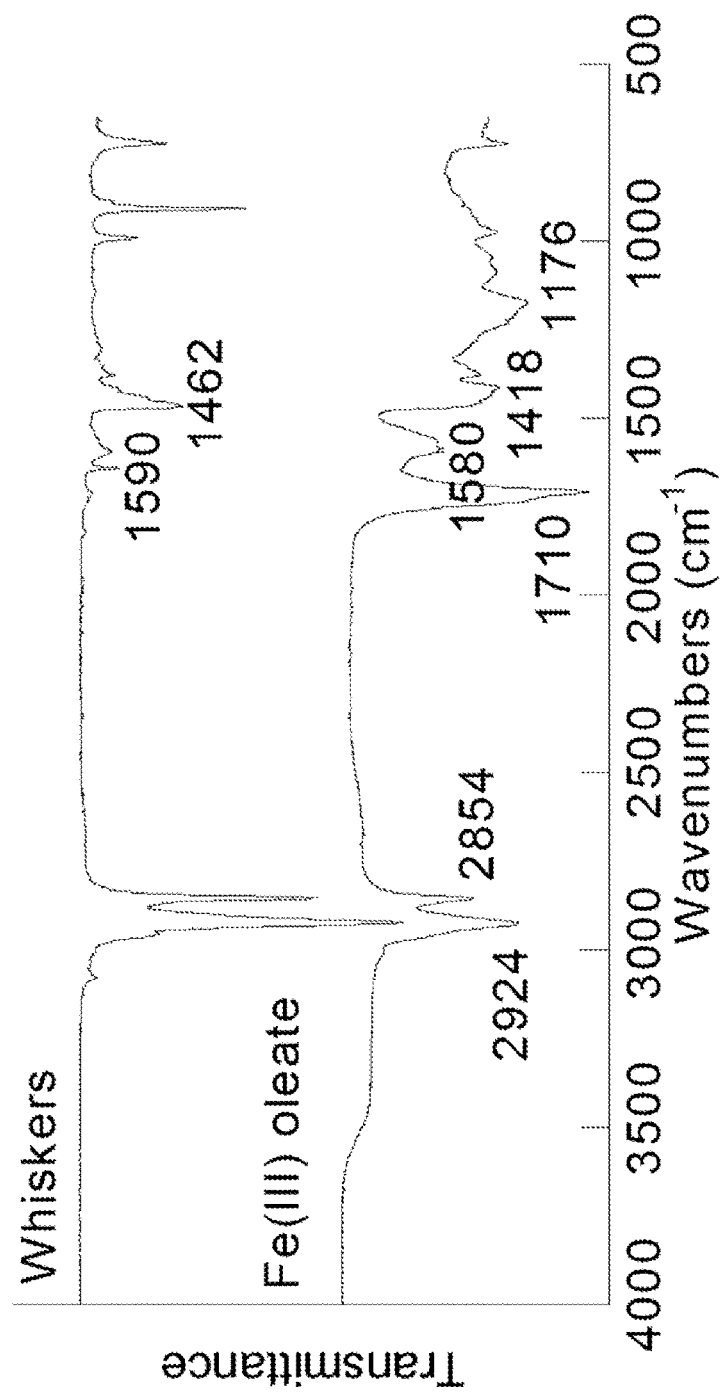
FIG. 5 illustrates FTIR spectra of an iron oleate complex precursor (bottom) and iron oxide nanowhiskers synthesized with OA (top).

The FTIR vibrational bands of carboxylic groups were utilized to study the surface coordination environments of the precursor complex and the nanowhiskers of the disclosure, as shown in FIG. 5. The frequency difference, $\Delta$, between the asymmetrical ($v_{as}$) and symmetrical ($v_s$) COO$^-$ vibration for a metal carboxylate complex indicates the nature of the coordination bonds, including monodentate ($\Delta=200\text{-}300$ cm$^{-1}$), bridging bidentate or ionic interactions ($\Delta=110\text{-}200$ cm$^{-1}$), and chelating bidentente ($\Delta<110$ cm$^{-1}$). The FTIR spectra of the iron oleate complex exhibited several characteristic IR bands of metal carboxylate, including 1710, 1580, 1418 and 1176 cm$^{-1}$. The band at 1710 cm$^{-1}$ can be assigned to either free oleic acid (Lu & Miller (2002) *J. Colloid and Interface Sci.* 256: 41-52) or the asymmetrical unidentate carboxylate (Hyeon, T. (2003) *Chem. Commun.* 927-934). The frequency difference of 162 cm$^{-1}$ between the two characteristic bands of the iron oleate complex (1580 and 1418 cm$^{-1}$) indicated the existence of a bridging coordination bond. The experimentally-estimated bridging bond mode can be understood by the binding energy differences of the bidentate bonds, according to the electronic structure calculations or the occurrence of multiple Fe nuclei species in the precursor. In contrast, the band at 1710 cm$^{-1}$ for iron oxide nanowhiskers disappeared, suggesting the remaining ligands were linked to the nanoparticle surfaces. The frequency difference of 128 cm$^{-1}$ also falls within the range of a bridging coordination bond, indicating little change in the ligand coordination environments during the nanowhisker formation.

A temperature-dependent study was performed to further understand the formation process of these nanowhiskers, in particular the role of the third ligand with stronger binding. A reaction conducted at 100° C. did not produce whisker-like morphology, forming dark pasty materials (FIG. 10A); while nanowhiskers were observed at 180° C. (FIG. 10B). The reaction at 230° C. produced a mixture of nanowhiskers and small irregular nanoparticles (FIG. 10C). The formation of the small irregular nanoparticles is likely due to the further decomposition of the remaining ligand. Finally, spherical nanoparticles were observed for a reaction conducted above 300° C. (FIG. 10D), as commonly reported in the literature. These observations indicate that the remaining third ligand is critical for the nanowhisker formation, because the third ligand could start decomposing above 200° C. according to the TGA plot shown in FIG. 2A).

To further investigate the role of the third ligand, the Fe(II) oleate and Fe(II)/Fe(III) oleate mixture were prepared in a similar way but with inert gas protection. TGA analyses of these complexes were performed at a heating rate of 5° C./min and nanoparticle synthesis using them as precursors. The TGA plot of the Fe(II) oleate showed a weight loss onset at about 185° C., but continued up to about 270° C., indicating a slow decomposition process. Compared to the TGA plot of the Fe(III) oleate complex, the secondary weight loss around 230° C. was not apparent (FIG. 11A), consistent with electronic structure calculations of the Fe(II) oleate complex, where the Fe(II) oleate complex has two stable structures with symmetric ligand arrangements (FIG. 6A). The symmetrical arrangements indicate similar binding energies or dissociation temperatures of these two ligands. A very small weight loss region right below 300° C. exhibit a slightly different weight loss rate, likely from the oxidation of Fe(II) oleate during synthesis or experimental operation. This oxidation process can also be visualized by the color change of the complex from dark to brown. The TGA plot of the Fe(II)/Fe(III) oleate complex mixture did not show much difference from the decomposition behavior of the Fe(III) complex (FIG. 11A) with two weight loss onsets below 300° C. TGA analyses were also performed on commercially available, stable Fe(II) and Fe(III) stearate complexes (FIG. 11B), where the difference in weight losses can be clearly seen with one weight loss onset for the Fe(II) complex and two for the Fe(III) complex below 300° C.

Comparable experiments were also performed using Fe(II) oleate and a Fe(II)/Fe(III) oleate mixture as precursors under similar conditions. Irregular shaped and somehow aggregated nanoparticles were observed when Fe(II) oleate was used as an precursor (FIG. 6B). In contrast, a mixture of small irregular nanoparticles and nanowhiskers was formed when using this complex mixture as the precursor under identical reaction conditions (FIG. 6C), indirectly confirming the importance of the third ligand in directing the growth of iron oxide nanowhiskers.

Figure 12B:
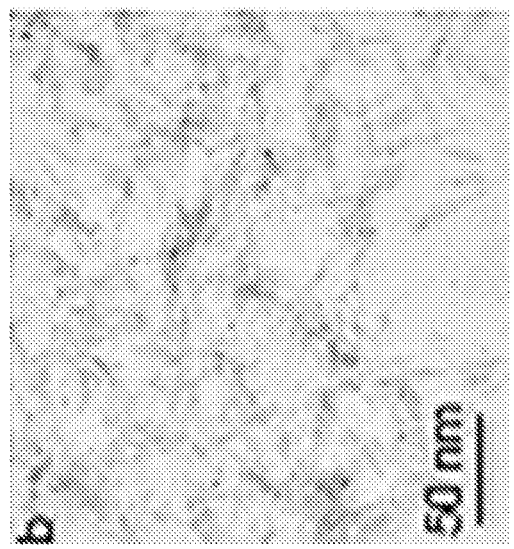
Figure 12A:
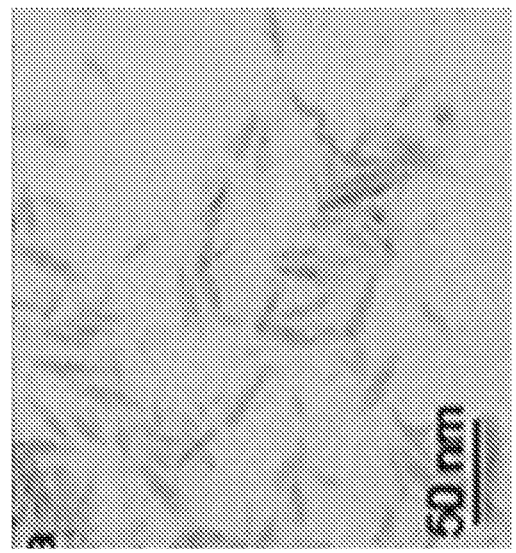
FIG. 12A is a digital image illustrating iron oxide nanowhiskers synthesized with OA and TOPO.

It is well known in the art that selective adsorption of ligands on the nanoparticle crystalline planes can significantly alter the growth pathways of nanoparticles, subsequently leading to the control of nanoparticle geometries (Hyeon, T. (2003) *Chem. Commun.* 927-934). Experiments using surfactant mixtures, therefore, were performed to determine the effects of alternate ligands on nanowhisker formation. The surfactant mixtures were oleic acid (OA)/trioctylphosphine oxide (TOPO) and OA/oleyamine (ON), where TOPO has a weaker binding to iron oxide nanoparticle surfaces than OA, while ON has a stronger binding (Palchoudhury et al., (2010) *J. Appl. Phys.* 107: 09B311-09B313). Both experiments produced nanoparticles with whisker morphologies, as shown in FIGS. 12A and 12B). The FTIR spectra of these nanowhiskers (shown in FIG. 12C) exhibited primarily the characteristic bands of carboxylates with no detectable signals of TOPO or ON. The frequency difference between the asymmetrical ($v_{as}$) and symmetrical ($v_s$) COO$^-$ vibrations for both samples also fell within the range of the bridging coordination mode, providing additional evidence that the remaining ligand of the iron oleate complex plays a critical role during the nanostructure formation and that the growth process was not altered by the other ligands.

Figure 13A:
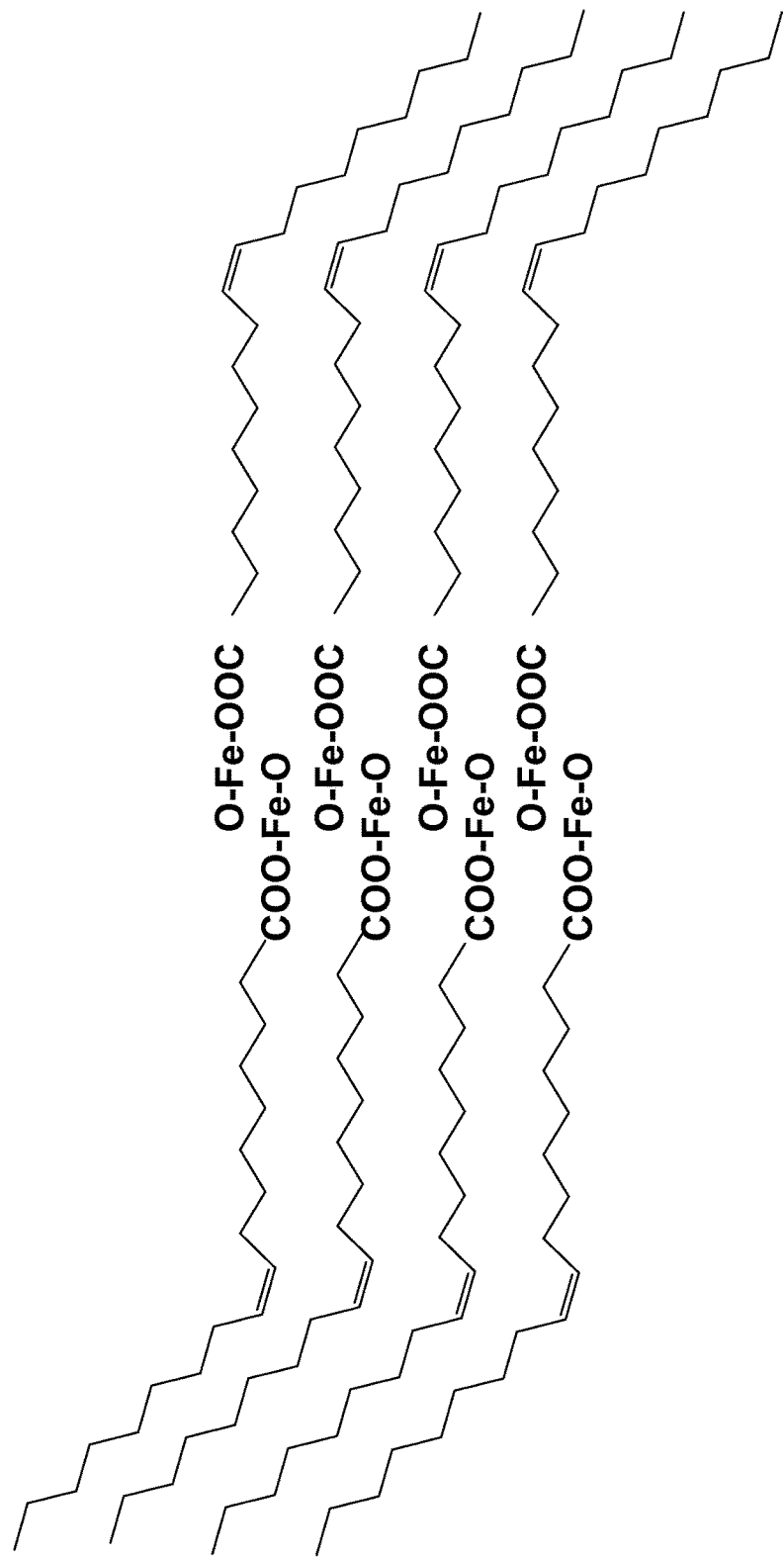
FIG. 13A is a schematic illustration of the iron oxide nanowhisker formation mechanism.

While not wishing to be bound by any one theory, based on all these observations, it is likely that the nanowhisker formation was directed by the third ligand. The interaction between the third ligand plays an important role in directing the formation of the ultrathin nanostructure, where the Fe—O part of the complex forms the inorganic backbone and surrounded by the oleate ligands (see FIG. 13A). Similar reactions were also performed at 230° C. using commercially available, stable precursors (e.g., Fe(II) and Fe(III) stearate complexes). Thus, similar results were obtained with the formation of spheres for Fe(II) stearate and ultrathin nanostructures for Fe(III) stearate, as shown in FIGS. 13B and 13C) but with cavities within the ultrathin nanostructures.

The fundamental building block of the nanowhiskers may be stable iron oxide nanoclusters with a ligand shell based on the diameter of the nanowhiskers. Iron oxide nanoclusters have been previously observed and exhibit magnetic transition characteristics of molecular magnets to bulk magnetism (Gatteschi et al., (1994) Science 265: 1054-1058; Canada-Vilalta et al., (2003) Inorg. Chem. 42: 7819-7829; Christmas et al., (1993) J. Am. Chem. Soc. 115: 12483-12490). It has been previously reported that iron carboxylate complexes could self-assemble into crystalline films by direct evaporation and without heat treatment (Popescu et al., (1996) Thin Solid Films 274: 143-146).

Accordingly, electronic structure calculations were performed on a hypothesized iron oxide nanocluster-oleate structure, $Fe_{39}O_{62}(HCOO)_{12}$ (FIG. 7A) to understand its structural geometry and stability. This structure has a 1.1 nm iron oxide nanocluster center with $S_6$ symmetry and a ligand shell. The ligands were simplified as HCOOH to reduce the workload from the long hydrocarbon chains (with an assumption that the chain length would only mildly affect the nanocluster geometry, at most). In the iron oxide nanocluster center, the 39 $Fe^{3+}$ cations occupy 8 tetrahedral sites and 7 octahedral sites in the inner core, and 12 pentahedral sites (blue) and 12 octahedral sites (blue) on the surface, forming 24 Fe—O coordinate bonds in a bridging mode with 12 $HCOO^-$ ligands. The bridging mode coordination bonds are consistent with the FTIR analysis of the oleate coated nanowhiskers, yielding a $RCOO^-$ to $Fe_2O_3$ ratio of 1:1.6. The bridging bonds of the relaxed structure (FIG. 7A) can be clearly identified. After relaxation, the oleate ligands were introduced to the nanocluster core to present the configuration of the ligand shell complex (FIG. 7B). It must be recognized that with a complex structure like that shown in FIG. 7A, optimization likely only leads to a local minimum when considering the complete three-dimensional phase space. The model, therefore, is a "relaxed" representation of the cluster.

The ratio of the ligands to $Fe_2O_3$ could be experimentally determined using a TGA measurement. The weight loss started around 200° C. and gradually continued to 400° C. The early weight loss can be ascribed to the decomposition of oleate, as suggested by the TGA plot of the oleate complex at a slower heating rate (1° C./min) (FIG. 2A). The weight loss above 300° C. is from desorption or vaporization of oleate ligands. This thermal behavior is similar to that of oleic acid-coated iron oxide nanoparticles (Huang et al., (2008) J. Phys. Chem. C 112: 15684-15690). The final residue mass of the TGA measurements was about 62% after heating-up to over 500° C., as shown in FIG. 7C.

The mass percentage divided by the molecular weight of $Fe_2O_3$ and the oleate ligand led to a molecular ratio of $RCOO^-$ to $Fe_2O_3$ of about 1:2.8. The ratio (1:1.6) of RCOO to $Fe_2O_3$ for the simulated nanocluster (1.1 nm) was larger than that of the experimental estimation (1:2.8) because the size of the simulated nanocluster was smaller than the diameter of the nanowhiskers. With increasing cluster size, the ratio of RCOO to $Fe_2O_3$ will decrease because of the decreasing surface atom percentage, which requires less ligands to saturate the surface Fe sites. The slightly reduced simulation model was chosen for computational efficiency.

Accordingly, the present disclosure encompasses thin iron oxide nanowhiskers and methods of manufacture thereof through selective decomposition of the iron oleate complex. Ligand coordination microenvironments play an important role in the nanowhisker formation. The different ligand environments were probed by electronic structure calculations and TGA measurement. A ligand-directed growth mechanism for the iron oxide nanowhisker formation was proposed; and stable iron oxide nanoclusters were selected to be the basic building blocks. Results from electronic structure calculations on a hypothesized nanocluster agreed well with our experimental observation. It is also contemplated that the methods of the present disclosure may be readily adapted for the synthesis of similar nanostructures using other metals by the selection of suitable ligands and decomposition temperatures are identified. The formation of the nanowhiskers provides a unique shape-control example of nanostructures based on understanding of the precursor ligand chemistry. In particular, the effects of the ligand microenvironment present another synthetic strategy for nanoparticle shape control.

One aspect of the disclosure, therefore, encompasses embodiments of methods for synthesizing ultrathin nanostructures, where the method can comprise the steps of: (a) obtaining a metallic core-ligand complex precursor comprising a metallic moiety and a plurality of ligands attached to said metallic moiety; and (b) incubating the metallic core-ligand complex precursor mix at an incubation temperature selected from the group of: from about 100° C. to about 300° C., from about 100° C. to about 200° C., from about 100° C. to about 175° C., from about 100° C. to about 150° C., about 300° C., about 250° C., about 230° C., about 225° C., about 200° C., about 180° C., about 175° C., about 170° C., about 150° C., and about 125° C., wherein said temperature is selected to generate a population of ultrathin nanostructures by a process of thermal displacement of some or all of the ligand moieties from the metallic core.

In some embodiments of this aspect of the disclosure, the step of obtaining a metallic core-ligand complex precursor can comprise mixing a metallic core, at least one ligand species, and an organic solvent, thereby forming a metallic core-ligand complex precursor:organic solvent mix.

In some embodiments of this aspect of the disclosure, the ultrathin nanostructures can have at least one dimension of about 1 nm to about 4 nm.

In some embodiments of this aspect of the disclosure, the ultrathin nanostructures can have at least one dimension of about 2 nm.

In embodiments of this aspect of the disclosure, the metallic core can be a magnetic ferrite-based moiety selected from ferric oxide, ferrous oxide, a ferric ion, a ferrous ion, a manganese ferrite, a zinc ferrite, a copper ferrite, a chrome ferrite, a cobalt ferrite, a nickel ferrite, a non-ferrous metallic ion, and any combination thereof.

In some embodiments of this aspect of the disclosure, the plurality of ligands attached to the metallic core-ligand complex can comprise at least one fatty acid species, at least one non-fatty acid species, or at least one fatty acid species combined with at least one non-fatty acid species In embodiments of this aspect of the disclosure, the at least one fatty acid species can be a long-chain saturated fatty acid, a long-chain mono-unsaturated fatty acid, and a long-chain unsaturated fatty acid.

In some embodiments of this aspect of the disclosure, the at least one fatty acid species can be myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, myristic acid, palmitic acid, stearic acid, arachidic acid, behenic acid, lignoceric acid, cerotic acid, eicosenoic acid, mead acid, and nervonic acid.

In some embodiments of this aspect of the disclosure, the at least one fatty acid is oleic acid.

In some embodiments of this aspect of the disclosure, the at least one non-fatty acid ligand can be oleic acid, tri-N-octylphosphine oxide (TOPO), oleylamine, a Good's buffer, biotin, dopamine, histamine, a liquid crystal molecule, or any combination thereof.

In some embodiments of this aspect of the disclosure, the step of obtaining a metallic core-ligand complex precursor can comprise incubating a ferrite, a ferric salt, a ferrous salt, or a non-ferrous salt, with oleic acid or a salt thereof.

In some embodiments of this aspect of the disclosure, the incubation temperature can be selected to form a nanostructure structure selected from the group consisting of: a nanowhisker, a nanotube, a nanorice, a nanocube, and a nanosheet.

In one embodiments of this aspect of the disclosure, the metallic core-ligand complex can comprise ferric oxide complexed with a plurality of oleic acid moieties, and wherein said complex is incubated in the organic solvent at about 150° C., thereby forming a population of nanowhiskers.

Another aspect of the disclosure encompasses embodiments of a nanostructure synthesized according to the methods of the disclosure.

Another aspect of the disclosure encompasses embodiments of a pharmaceutically acceptable composition comprising a nanostructure synthesized according to the methods of the disclosure and a pharmaceutically acceptable carrier.

In some embodiments of this aspect of the disclosure, the pharmaceutically acceptable composition formulated to provide a high-contrast magnetic resonance image of a recipient animal or human subject.

Still another aspect of the disclosure encompasses embodiments of an ultrathin nanostructure that comprises a metallic core, the ultrathin nanostructure having at least one dimension of about 1 nm to about 4 nm and a substantially reduced relaxivity compared to a nanostructure having dimensions of at least 4 nm.

In some embodiments of this aspect of the disclosure, the ultrathin nanostructure can have at least one dimension of about 2 nm or less.

In some embodiments of this aspect of the disclosure, the metallic core can be a magnetic ferrite-based moiety selected from the group consisting of: a ferric oxide, a ferrous oxide, a ferric ion, a ferrous ion, a manganese ferrite, a zinc ferrite, a copper ferrite, a chrome ferrite, a cobalt ferrite, and a nickel ferrite.

In some embodiments of this aspect of the disclosure, the ultrathin nanostructure can be a nanowhisker, a nanotube, a nanorice, a nanocube, or a nanosheet.

In some embodiments of this aspect of the disclosure, the ultrathin nanostructure can further comprise a biocompatible coating.

In some embodiments of this aspect of the disclosure, the ultrathin nanostructure can further comprise a targeting ligand disposed on the surface of the ultrathin nanoparticle.

In some embodiments of this aspect of the disclosure, the ultrathin nanostructure can further comprise at least one of the group consisting of: polyacrylic acid (PAA), polyethyleneimine (PEI), glutathione (GSH), lactobionic acid (LBA), histamine, dopamine, L-DOPA, and biotin disposed on the ultrathin nanostructure.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Synthesis of the Fe (III) Oleate Complex.

The iron oleate complex of the disclosure was produced using a published procedure (Park et al., (2004) *Nat. Mater.* 3: 891-895, incorporated herein by reference in its entirety) with modifications. Briefly, potassium oleate (192.4 g) was mixed with ferric chloride (13 g) in a solvent mixture (hexane, 280 mL and ethanol, 160 mL) at 70° C. for four hours. The mixture was then phase-separated in a separation funnel. The organic phase containing iron oleate complex was then washed with de-ionized water and dried inside a chemical hood at room temperature. The entire process was performed in air without inert gas protection.

Example 2

Synthesis of the Fe(II) Pleate and Fe (III)/Fe(II) Oleate Complexes.

Figure 17:
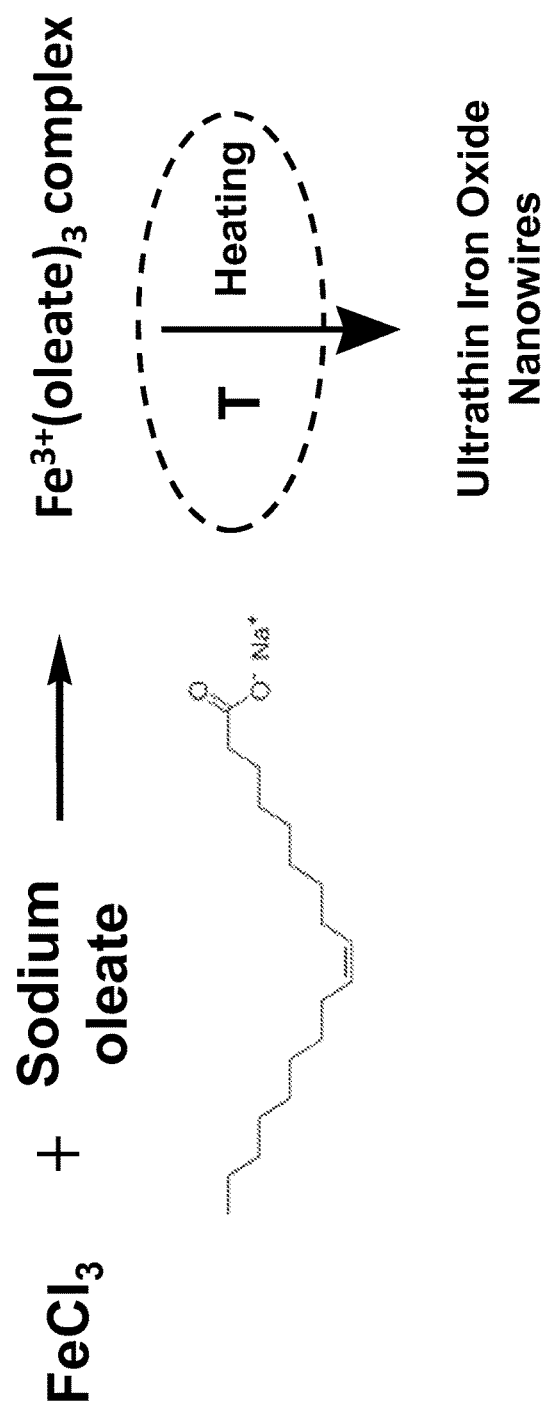
FIG. 17 schematically illustrates a method of the disclosure for the synthesis of ultrathin nanowires (nanowhiskers).
Figure 18B:
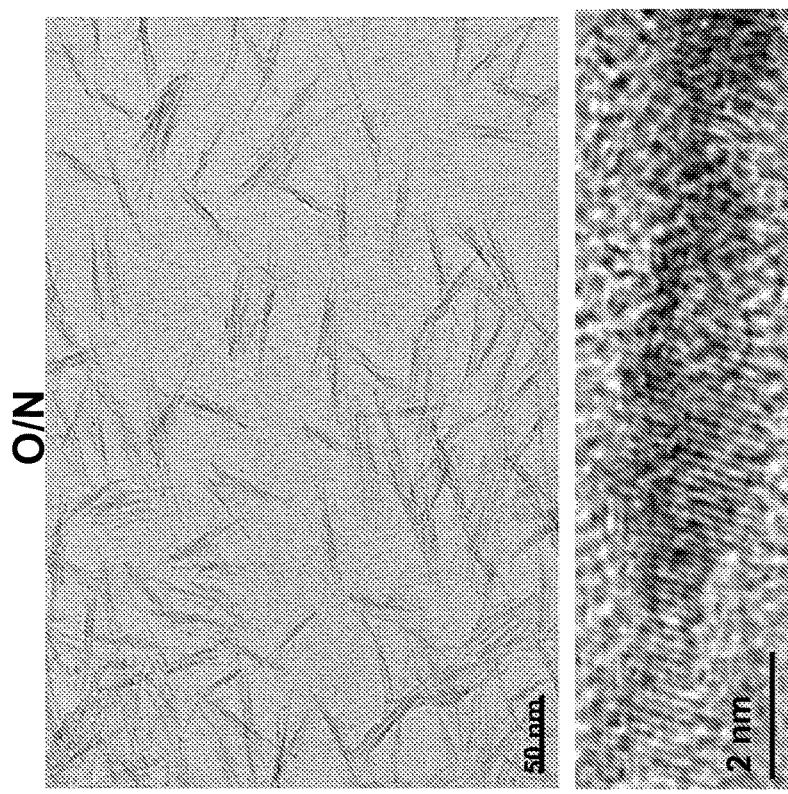
FIGS. 18A and 18B are digital images of ultrathin iron oxide nanostructures manufactured according to a method of the disclosure, with heating for 2.5 hrs (FIG. 18A) or overnight (FIG. 18B).
Figure 18A:
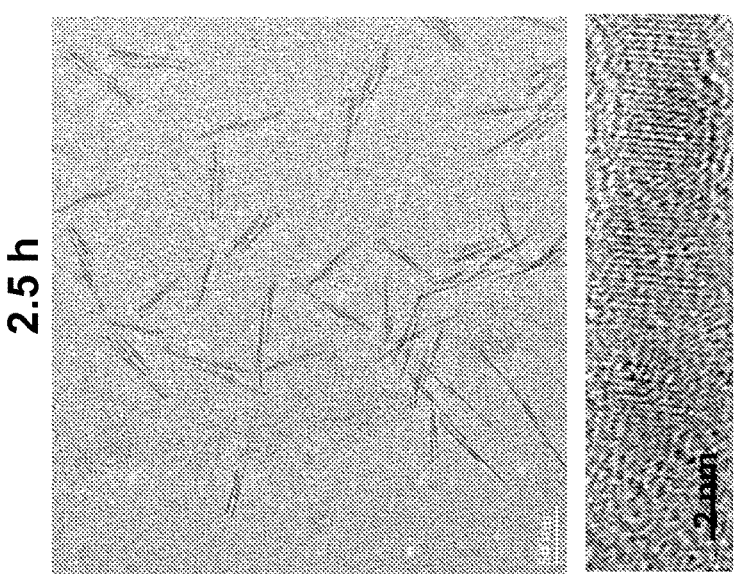
Figure 19B:
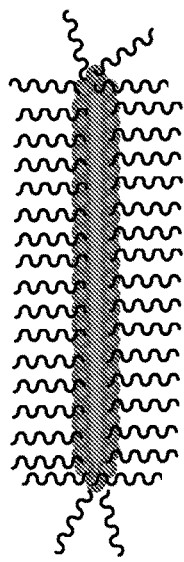
FIG. 19B schematically illustrates an ultrathin nanowire according to the disclosure.
Figure 19C:
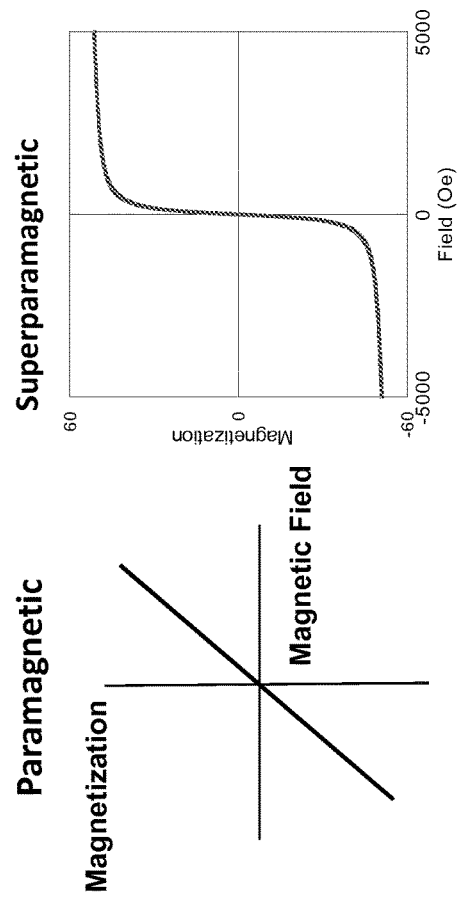
FIG. 19C are graphs illustrating the magnetic properties of an ultrathin nanowire according to the disclosure.
Figure 19A:
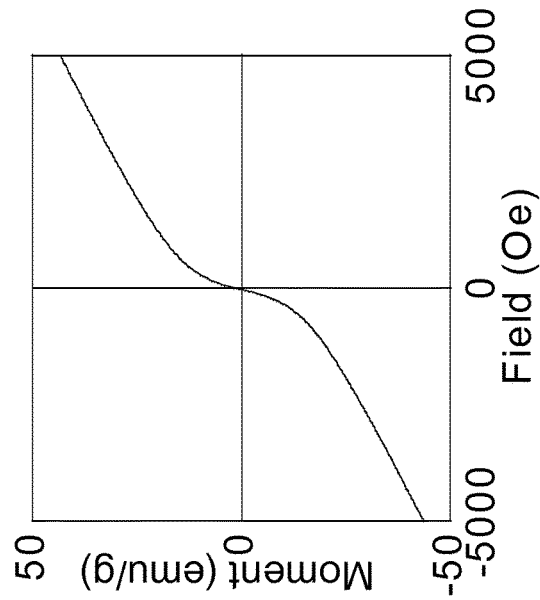
FIG. 19A is a graph illustrating the magnetic properties of an ultrathin nanowire according to the disclosure.

The Fe(II) oleate and the Fe(III)/Fe(II) oleate complex mixture were prepared for the formation of nanowhiskers. Specifically, Fe(III) chloride (4.3 g) and Fe(II) chloride (1.69 g, $Fe^{3+}/Fe^{2+}=2:1$) or Fe(II) chloride (5.07 g) were reacted with the sodium oleate (36.5 g) in a solvent mixture (hexane-140 mL, ethanol-80 mL, and water-60 mL) at 60° C. for four hours, as schematically shown in FIG. 17. The mixture was processed in the same way as the Fe(III) oleate complex. However, the entire process was performed under an argon atmosphere to prevent the oxidation of Fe(II).

Example 3

Electronic Structure Calculations of the Iron Oleate Complex.

The optimal geometric structures of Fe(III) and Fe(II) oleate complexes were predicted with electronic structure calculations using GAUSSIANO3™ (Gaussian, Inc. Wallingford, Conn.). The geometric optimization of the complexes was performed using all-electron density-functional theory (DFT) with the B3LYP (Becke, three-parameter, Lee-Yang-Parr) (Lee et al., (1988) *Phys. Rev. B* 37: 785-789; Becke, A. D. (1993) *J. Chem. Phys.* 98: 5648-5652) hybrid exchange-correlation functional and 6-31+G(d) basis set (Ditchfield et al., (1971) *J. Chem. Phys.* 54: 5; Rassolov et al., (2001) *J. Comput. Chem.* 22: 976-934, incorporated herein by reference in their entireties). Diffuse functions were exclusively applied to Fe and O in the carboxyl groups, in which electron lone pairs play a key role in the formation of coordination bonds. The binding energies (BEs) of the first, second, and third ligand of the iron oleate complex were defined as: $BE_1=[E_{Fe(OA)3}-(E_{Fe(OA)+2}+E_{OA-})]$, $BE_2=[F_{e(OA)+2}-(EF_{e(OA)2+1}+E_{OA-})]$ and $BE_3=[EF_{e(OA)2+1}-(EF_{e3}++E_{OA-})]$, and, where E is the energy of an isolated species in the gas phase. Hence, negative (positive) BEs denotes an exothermic (endothermic) binding process. An iron oxide nanocluster model, $Fe_{39}O_{62}(HCOO)_{12}$, was built and optimized using the B3LYP functional, with an STO-3G basis set for C, H, and O, and an LANL2DZ effective core potential for Fe. This iron oxide nanocluster has a $(Fe_2O_3)_x$ center with a diameter of 1.1 nm and an oleate ligand shell, where the iron oxide center has a spinel structure with S6 symmetry, similar to that of maghemite iron oxide nanoparticles.

Example 4

Thermogravimetric Analysis (TGA).

TGA measurements were conducted to study the thermal decomposition behavior of Fe(III) oleate, Fe(II)/Fe(III) oleate, and the iron oxide nanowhiskers. Specifically, TGA experiments were performed on a TA Instruments TGA 2950 thermogravimetric analyzer (New Castle, Del.) under a nitrogen atmosphere at a constant heating rate of 1 or 5° C. min−1 from room temperature to 500° C. The isothermal analysis was conducted by first heating the sample to 80° C. for 30 min to remove moisture, followed by 3.5 hours of heating at 150° C. The use of inert gas protection was important for avoiding any premature oxidation and/or ligand combustion.

Example 5

Synthesis of Iron Oxide Nanowhiskers.

Iron oxide nanowhiskers were synthesized by heating the iron oleate complex (1.8 g) in 1-octadecene (13 mL) at 150° C. in the presence of non-fatty acid ligands (0.3 mL OA, 0.1 OA mL/0.2 g TOPO, or 0.1 mL OA/0.2 mL ON). The reaction was kept at the reaction temperature for 2.5 hours under an argon atmosphere. Nanoparticle syntheses using Fe(II) oleate, Fe(II)/Fe(III) oleate mixture, Fe(II) stearate, and Fe(III) stearate as precursors were performed under similar conditions using OA only as the ligand. The reaction temperature was set at 230° C. for stearate reactions, and 185° C. for Fe(II) oleate reaction, instead 150° C. based on the TGA analysis.

Example 6

Characterization of Iron Oxide Nanowhiskers.

The size, structure, and morphology of iron oxide nanowhiskers were examined on a FEI Technai F-20 TEM. The magnetic properties were studied on a Princeton Alternating Gradient Magnetometer (AGM). Fourier Transform Infrared (FTIR) spectra of the iron oleate complex and the ligand-coated nanowhiskers were collected in order to understand the binding environment. The FTIR studies were performed on a PerkinElmer Spectrum 100 FT-IR spectrometer (Bucks, UK), equipped with an attenuated total reflectance (ATR) cell by accumulation of 4 scans, with a resolution of 2 cm−1. The Fe valance states of the iron oxide nanowhiskers were studied using x-ray photoelectron spectroscopy (XPS) on a Kratos AXIS 165 Multitechnique Electron Spectrometer, equipped with a monochromatic x-ray source (Al, hv=1486.6 eV). The Raman spectrum of iron oxide nanowhiskers were collected using a Bruker Senterra system (Bruker Optics Inc. Woodlands, Tex.) equipped with 785 nm laser source at 10 mW laser power and 20× objective.

Example 7

TGA Analysis of the Iron Oleate Complex:

A TGA measurement were conducted at a constant heating rate of 1° C. min−1 from room temperature to 500° C. to compare the heating rate effects on the decomposition process of the iron oleate complex (FIG. 2A). Further, an isothermal analysis was performed by first heating the sample to 80° C. for 30 min to remove moisture, followed by 3.5 hours of heating at 150° C. (FIG. 2B).

The TGA plot for the slower heating rate demonstrated the same weight loss onset at around 150° C., but it continued until 200° C., indicating a slow decomposition process of the two weakly-bound ligands. The isothermal analysis performed at 150° C. reached a constant weight loss of 9% after approximately 2.5 hours, and contiguous weigh loss was not observed, suggesting the remaining ligands are stable at this temperature.

Example 8

XRD Scan of Iron Oxide Nanowhiskers:

The crystal structure of the nanowhiskers in powder form was studied on a Bruker AXSD8 Advanced x-ray diffractometer (XRD) using a Co source (Kα, λ=1.79 Å). The x-ray diffraction scan (FIG. 8) did not allow us to confirm the crystal phases of these nanowhiskers, magnetite or maghemite, due to the significant size broadening. However, the noticeable peaks at 35.1°, 41.4°, and 50.4° can be indexed as (220), (311), and (400) crystal planes of the iron oxide structures.

Example 9

Time-Dependent Study:

To monitor the structural evolution of the iron oxide nanowhiskers, intermediate samples were collected and examined using TEM without any washing. FIGS. 9A and 9B show the TEM images of samples at reaction time of 1 (FIG. 9A) and 1.5 hours (FIG. 9B).

Example 10

Temperature-Dependent Study:

The TGA measurements and the calculated binding energies of the Fe(III) oleate complex both suggest that the reaction temperature is a critical parameter for the nanowhisker formation. The decomposition of the more weakly-bound ligands was in the range of 150° C.-200° C. according to the TGA plot. Therefore, reactions were conducted at temperatures below, above, and within this range to investigate the temperature effects on the nanowhisker formation. Reactions at 80° C., 100° C., and 120° C. did not produce whisker-like morphology; instead, dark pasty materials were observed. FIG. 10A shows the TEM image of a sample generated at 100° C. Reactions performed at 140° C., 160° C. and 180° C. all produced nanowhiskers, similar to the nanowhiskers synthesized at 150° C. FIG. 10B shows the TEM image of a sample generated at 180° C. The reaction performed at 230° C. produced nanowhiskers with broken pieces, forming small irregular nanoparticles (FIG. 10C).

This tendency is likely due to the further decomposition of the remaining ligand. Further, spherical nanoparticles were observed for a reaction conducted above 300° C., as commonly reported in the literature and as shown in FIG. 10D. Therefore, nanowhisker formation can only be achieved when the reaction temperature is high enough to dissociate the two more weakly-bound ligands, but low enough to keep the third ligand attached.

Example 11

Figure 11B:
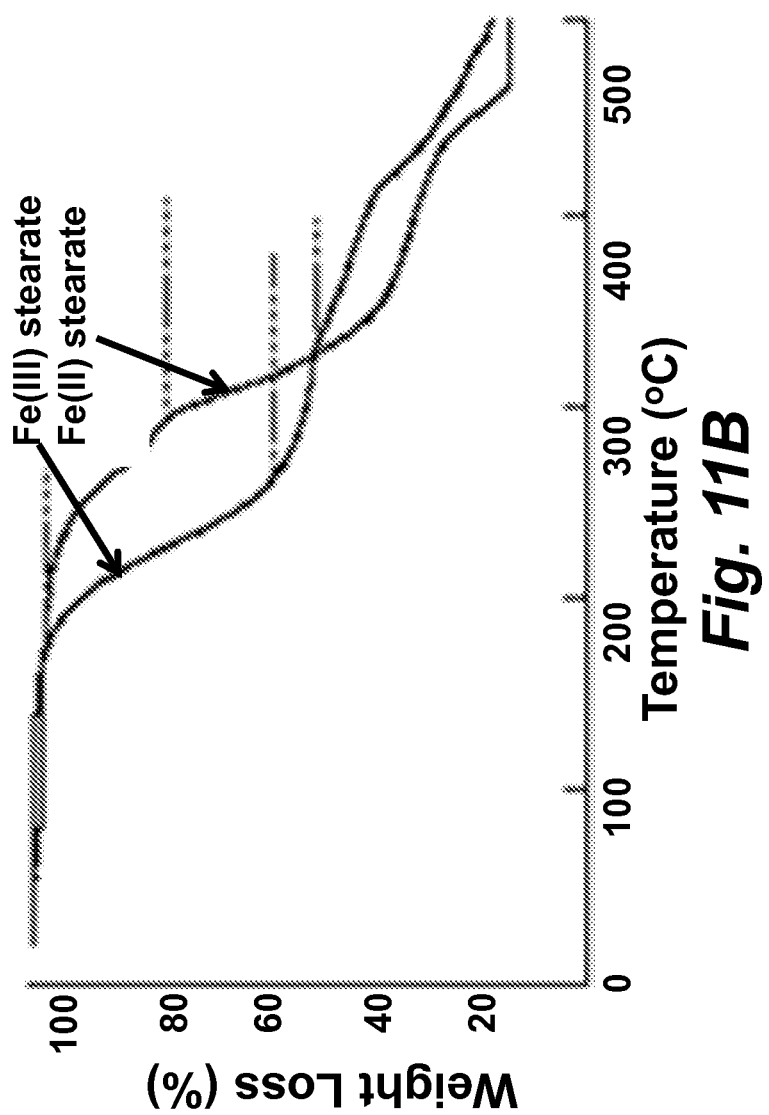
FIG. 11B is a graph illustrating a TGA plot of Fe(II) and Fe(III) stearate.

TGA Analysis of Fe(II) Oleate and Fe(III)/Fe(III) Oleate Complex Mixture:

TGA analyses of Fe(II) and Fe(II)/Fe(III) oleate complex mixture at a heating rate of 5° C./min were also conducted (FIG. 11A). The TGA plot of Fe(II) oleate showed similar weight loss onset to Fe(III) oleate complex, but without evident second weight loss around 230° C. A very small weight loss region right below 300° C. showed a different rate, which is likely from the possible oxidation of Fe(II) oleate during synthesis or experimental operation. Alternatively, we also performed TGA analyses on commercially available, stable Fe(II) and Fe(III) stearate complexes (FIG. 11B), where the difference in weight losses can be clearly seen with one weight loss onset for the Fe(II) complex and two for the Fe(III) complex below 300° C.

Example 12

Effects of Alternative Ligands:

Selective adsorption of ligands on the nanoparticle crystalline planes can significantly alter the growth pathways of nanoparticles, subsequently leading to the control of nanoparticle geometries. Experiments using surfactant mixtures (OA/TOPO and OA/ON) were performed to investigate the role of alternate ligands on the nanowhisker formation. The obtained nanostructures were then compared with the results from the OA-ligand-only reaction (the normal reaction condition). The overall ratio of the ligand to the iron precursor was kept the same for all of the reactions.

Figure 12C:
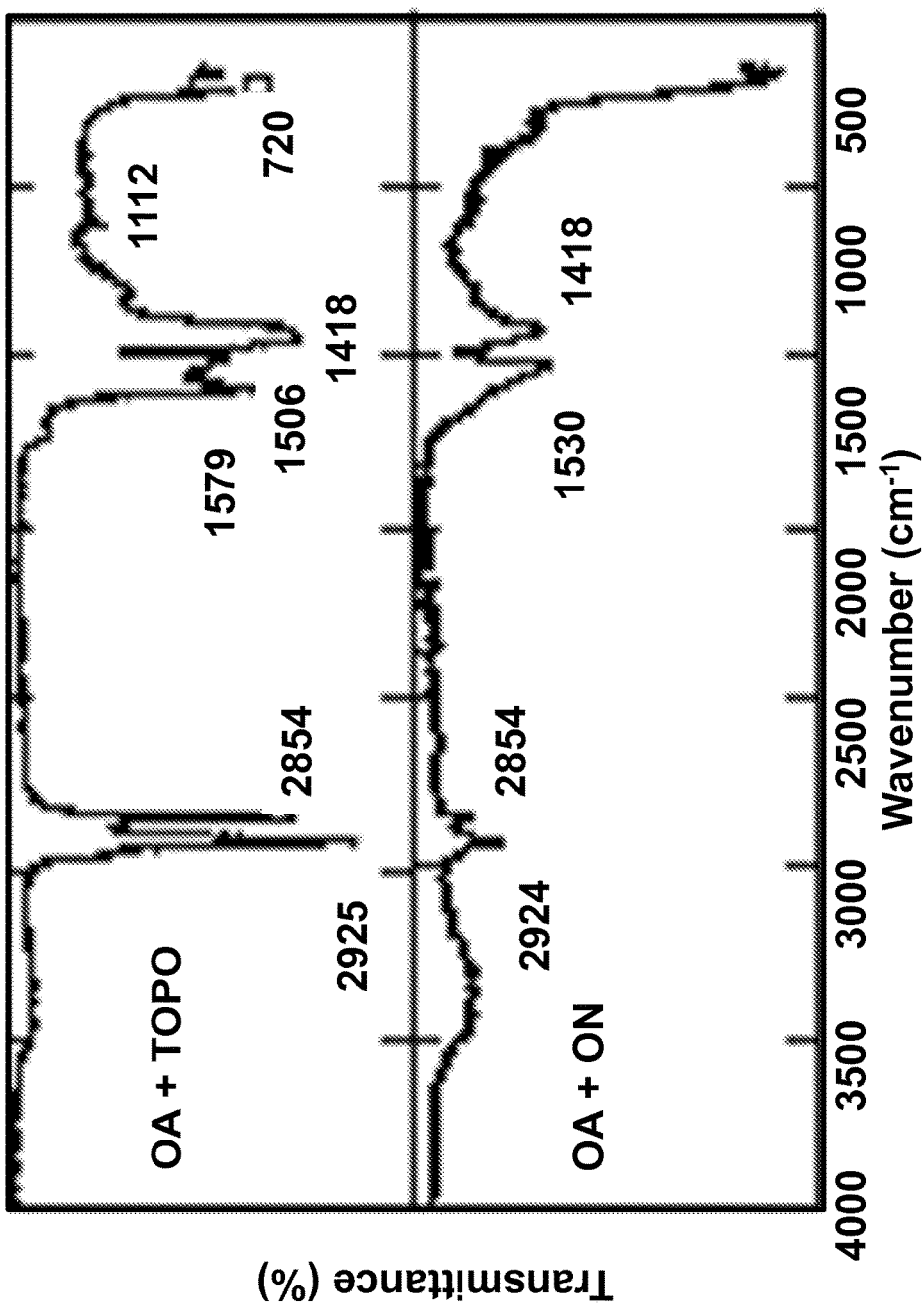
FIG. 12C illustrates FTIR spectra of iron oxide nanowhiskers synthesized with OA and TOPO (top) and iron oxide nanowhiskers synthesized with OA and ON (bottom).

Both experiments produced nanoparticles with whisker morphologies (FIGS. 12A and 12B). The FTIR spectra of these nanowhiskers did not show detectable signals of TOPO or ON, and the FTIR spectra were similar to the spectrum of the OA-only sample (FIG. 12C). The frequency difference between the asymmetrical (vas) and symmetrical (vs) COO-vibrations for both samples fell within the range of the bridging coordination mode. These observations provide additional evidence that the remaining ligand of the iron oleate complex plays a critical role during the nanostructure formation and that the growth process was not altered by the other ligands.

Example 13

Growth Mechanism of Iron Oxide Nanowhiskers:

The formation of iron oxide nanowhiskers can be a result of remaining ligand interactions, as illustrated schematically in FIG. 13A, where the interaction between the remaining ligands chains played an important role in directing the nanostructure growth. Additionally, to verify our hypothesis, we performed similar reactions at 230° C. using commercially available, stable precursors (e.g., Fe(II) and Fe(III) stearate complexes). Interestingly, very similar results were obtained with the formation of spheres for Fe(II) stearate and ultrathin nanostructure for Fe(III) stearate (FIGS. 13B and 13C). However, the presence of cavities within the ultrathin nanostructures need further investigation.

Example 14

Relaxivity Test on the Iron Oxide NPs with Different Shapes and Surface Coating Effects: General Findings:

The relaxivities of three types of iron oxide nanoparticles with similar inorganic core sizes, (e.g., iron oxide nanospheres, iron oxide nanocubes, manganese ferrite nanocubes) were tested.

TABLE 1

Magnetic property, r1, r2 relaxivity and r2/r1 ratios of different shaped nanoparticles

| Nanoparticles | Magnetic Property | $r_1$ $(mM^{-1}s^{-1})$ | $r_2$ $(mM^{-1}s^{-1})$ | $r_2/r_1$ |
|---|---|---|---|---|
| Spheres | Superparamagnetic | 9.3 | 214.8 | 23.1 |
| Cubes | Superparamagnetic | 7.6 | 146.7 | 19.3 |
| Plates | Super- + Para-magnetic | 6.9 | 22.8 | 3.3 |
| Whiskers | Super- + Para-magnetic | 7.1 | 14.8 | 2.1 |

All the nanoparticle water dispersions are very stable, leading to a perfect linear correlation of the relaxivity to nanoparticle concentration. The same nanoparticles at the same iron concentration, if an aggregation processes is induced by addition of salts, an increase of the relaxivity $r_2$ was observed, indicating the importance of measuring the relaxivity of nanoparticle-based contrast agents in biological relevant solution to mimic the application conditions.

Example 15

Figures 14A, 14B:
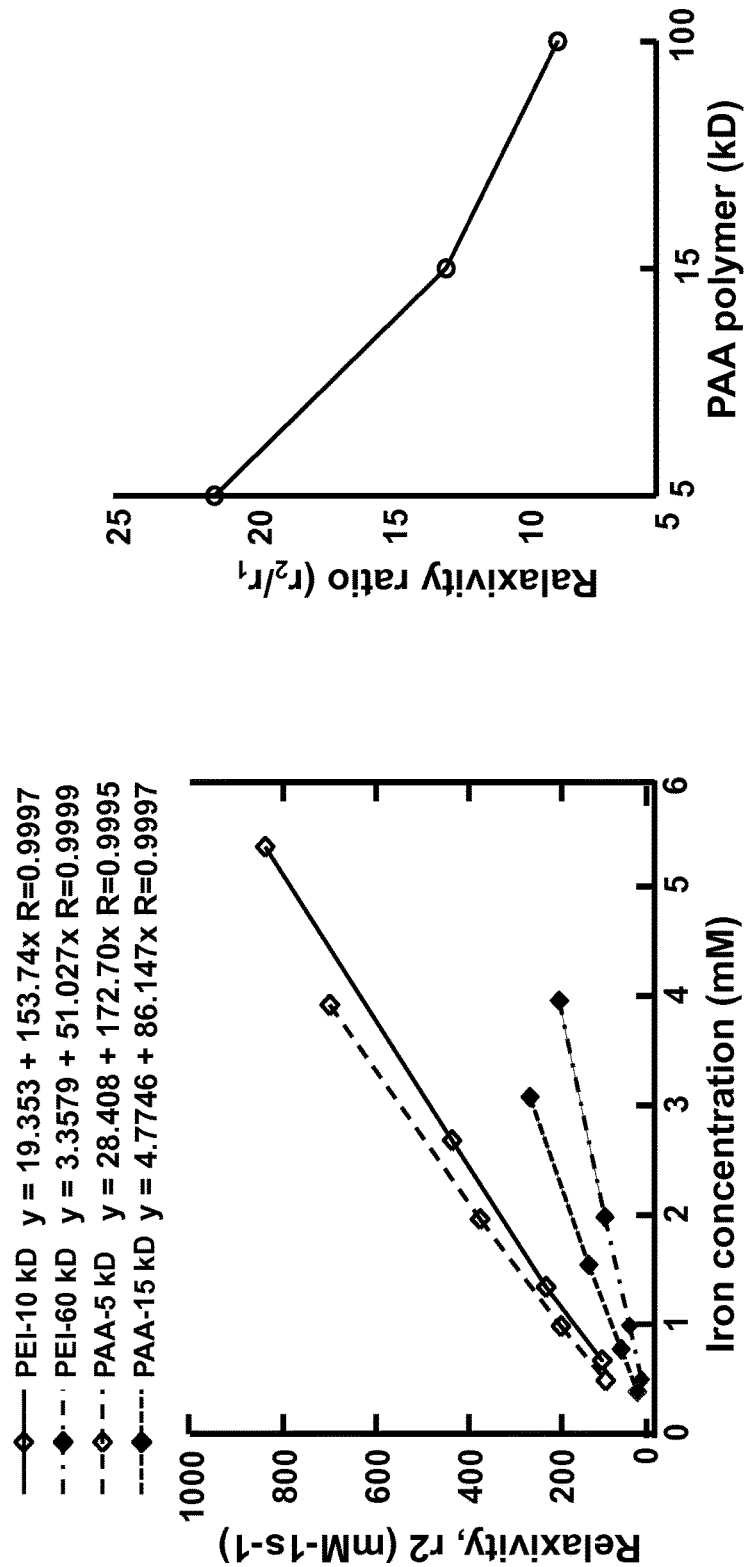
FIG. 14A is a graph illustrating the relaxivities, $r_2$, of PAA- and PEI-coated iron oxide NPs.
FIG. 14B is a graph illustrating the relaxivity ratios, $r_2/r_1$ of PAA polymers (5, 15, 100 kD).

Surface Coating Effects:

Initial relaxivity tests were also performed on PAA- and PEI-coated iron oxide NPs with different surface coating thickness (e.g., PAA-5, 15 kD; PEI-10, 60 kD). It was observed that a strong coating thickness effects the relaxivity, $r_2$, indicated by the slope of the relaxivity versus iron concentration plot, as shown in FIG. 14A. The relaxivity of the PEI (10 kD)-coated NPs, 153.74 $mM^{-1}$ $s^{-1}$ is three times higher than that of PEI (60 kD)-coated NPs, 51.027 $mM^{-1}$ $s^{-1}$. The relaxivities of PAA-coated NPs decreased from 172.70 $mM^{-1}$ $s^{-1}$ for 5 kD polymer to 86.147 $mM^{-1}$ $s^{-1}$ for 15 kD polymer. Further, significant drops in the $r_2/r_1$ ratios were observed for PAA-coated NPs of different coating thickness (PAA, 5 kD-21.3, PAA, 15 kD-12.75, 100 kD-8.64 mM$^{-1}$ s$^{-1}$, FIG. 14B). These initial studies suggest that the surface coating thickness directly influence the relaxivity.

Example 16

Figure 15B:
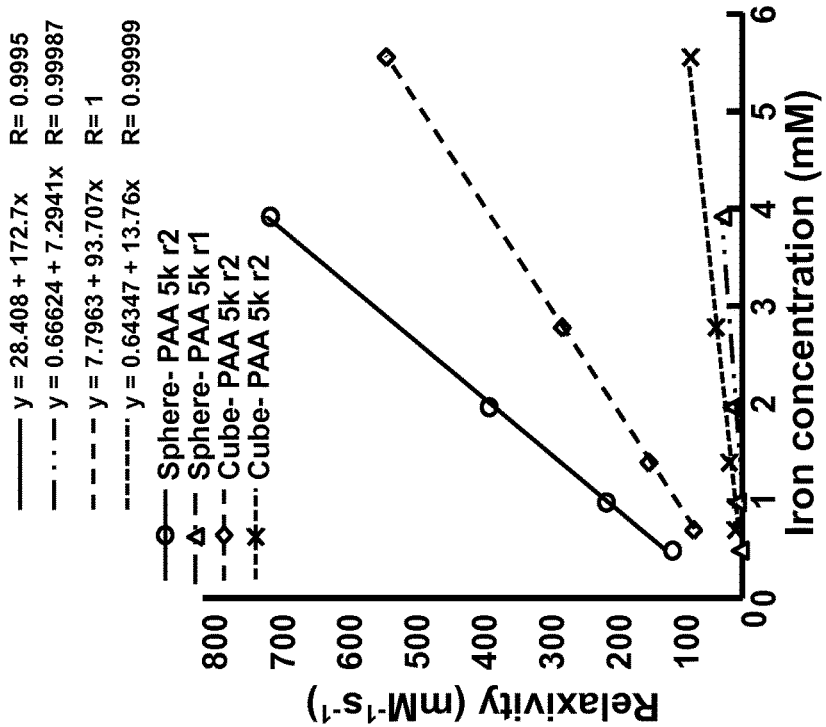
FIG. 15B is a graph illustrating shape-dependent relaxivities of PAA (5 kD)-coated spheres and nanocubes.
Figure 15A:
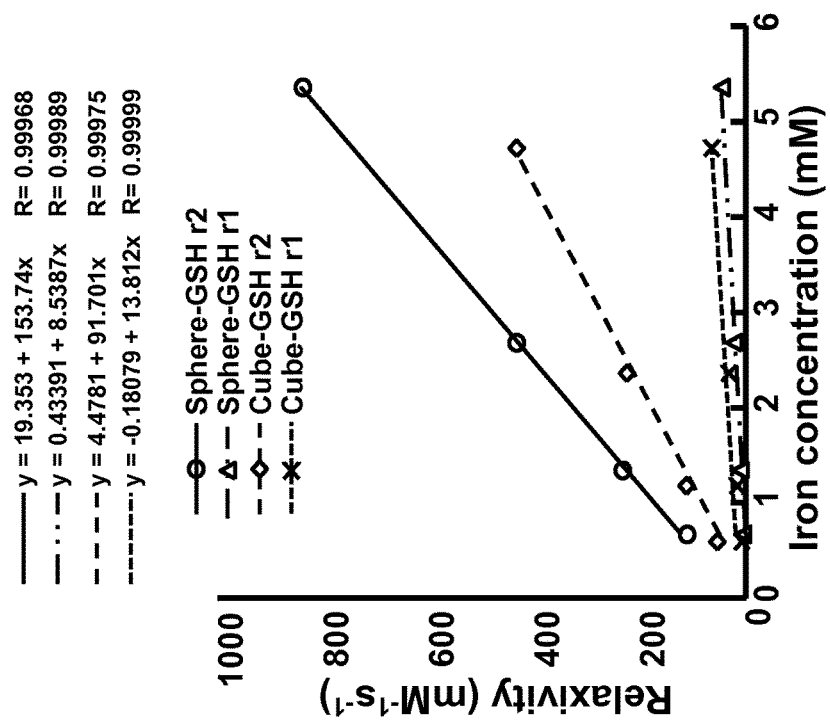
FIG. 15A is a graph illustrating shape-dependent relaxivities of glutathione (GSH)-coated spheres and nanocubes.

Shape Effects:

Two types of nanoparticles with similar surface to volume ratios, iron oxide nanospheres and iron oxide nanocubes were systematically compared. The relaxivity r$_2$ of the spheres was higher than that of the nanocubes regardless the surface coating type and thickness. However, the relaxivity r$_1$ of spheres was lower than that of the nanotube (FIGS. 15A and 15B), important to design highly efficient contrast agents for MRI.

Example 17

Doping Effects:

Relaxivity measurements on manganese ferrite nanocubes were also performed. Based on an elemental analysis, the doping level of the manganese was about 15%, which is close to half of the theoretical values. These low numbers of doping actually decreased the relaxivity r$_2$ and r$_1$, as shown in FIGS. 16A and 16B.

Example 18

Figure 20A:
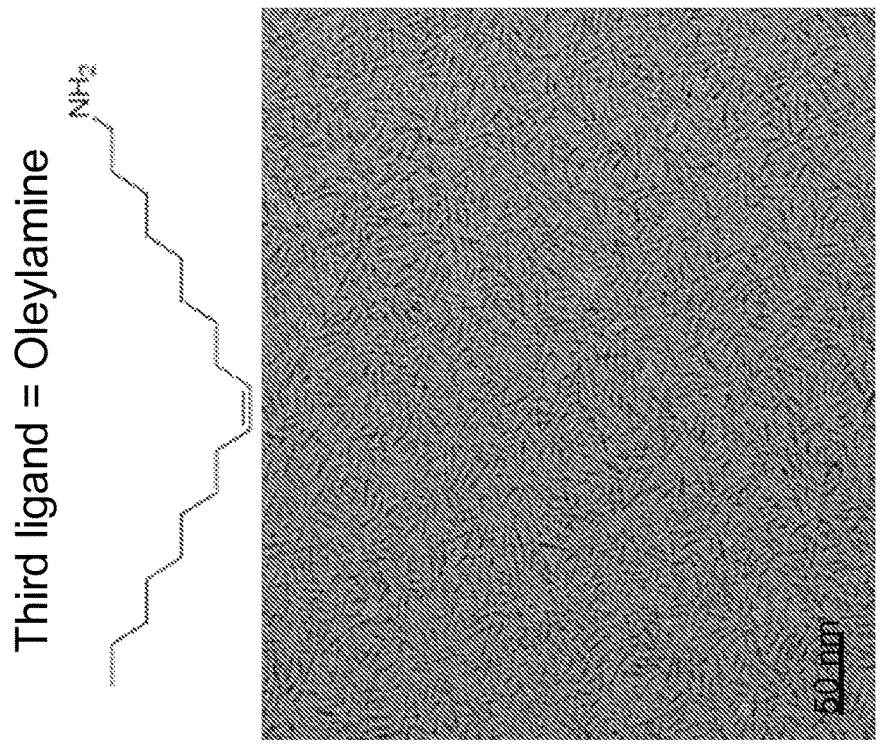
FIG. 20A schematically illustrates predictions of variations in precursor structures due to variation in ligands.
Figure 20B:
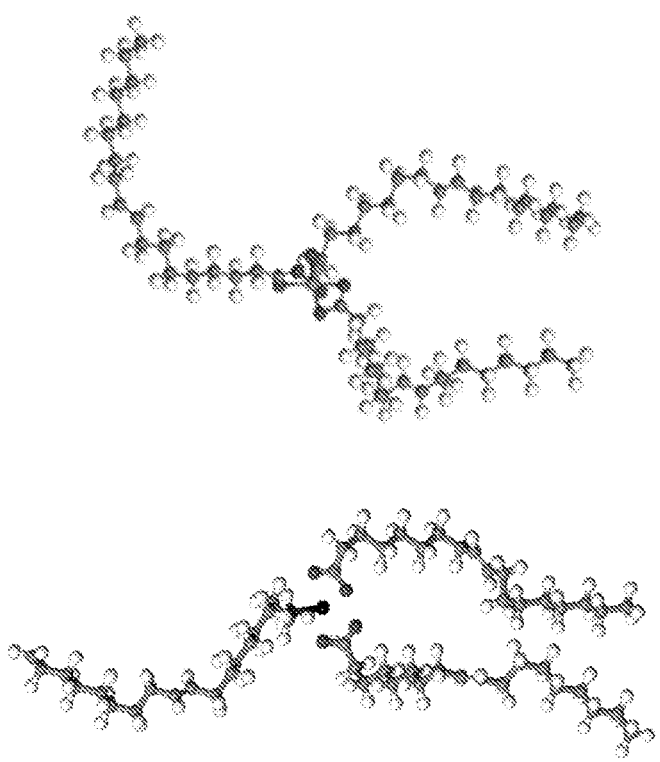
FIG. 20B illustrates nanowhisker formation by the methods of the disclosure using oleylamine as a ligand.
Figure 21:
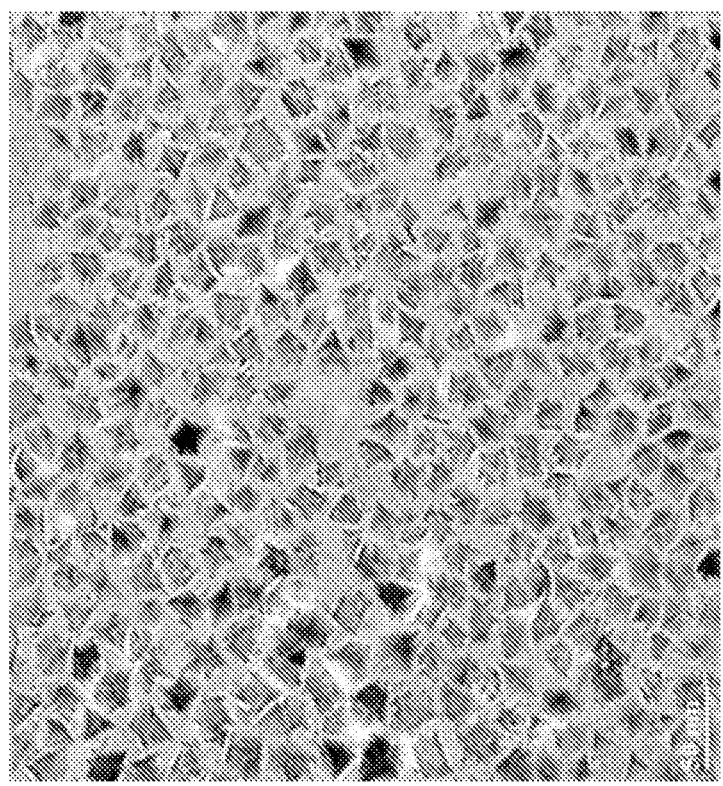
FIG. 21 is a digital image of iron oxide nanoplates synthesized according to the methods of the disclosure.
Figure 22B:
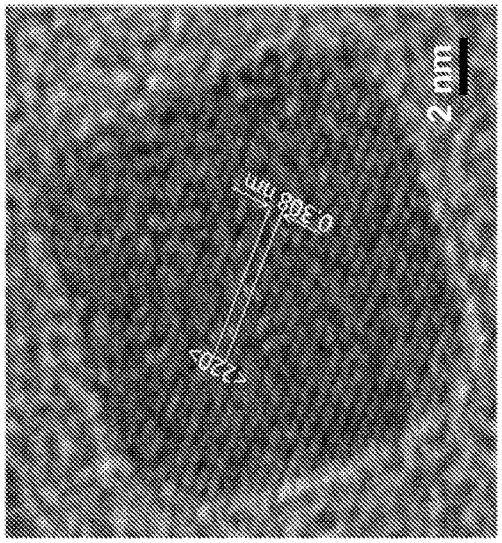
FIGS. 22A-22C illustrate manganese ferrite nanoplates (FIG. 22A) (and an enlargement of one nanoplate, FIG. 22B) formed from the precursor shown in FIG. 22C.
Figure 22C:
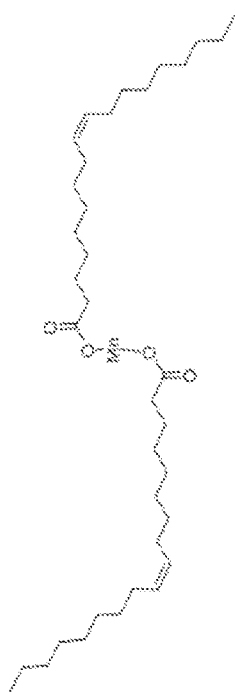
Figure 22A:
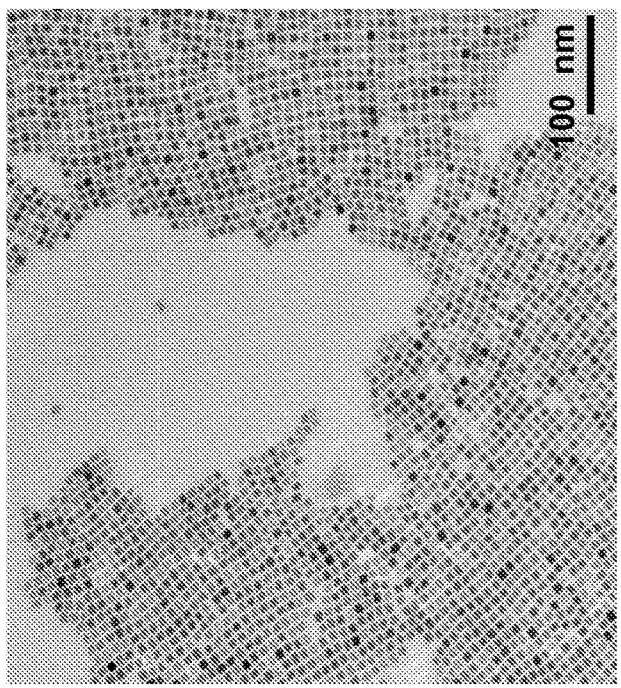
Figure 23A:
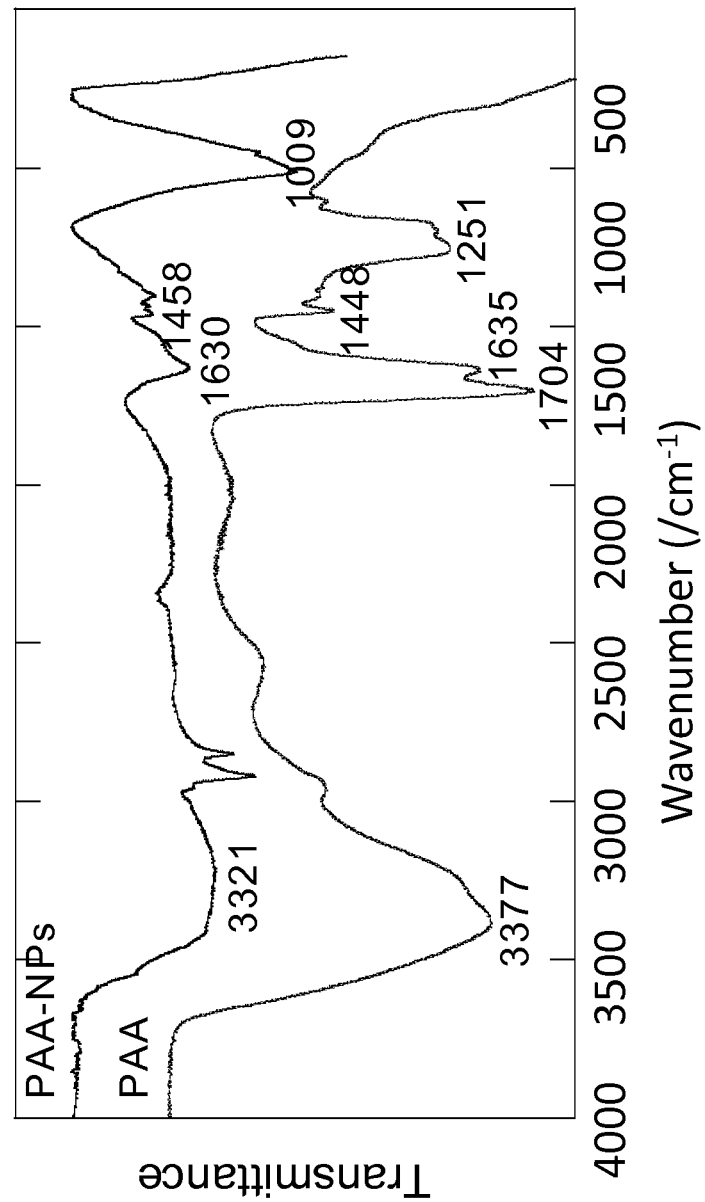
FIG. 23A is an FTIR spectrum of polyacrylic acid (PAA) attached to a nanoparticle of the disclosure (top) and polyacrylic acid (PAA) (bottom).
Figure 23B:
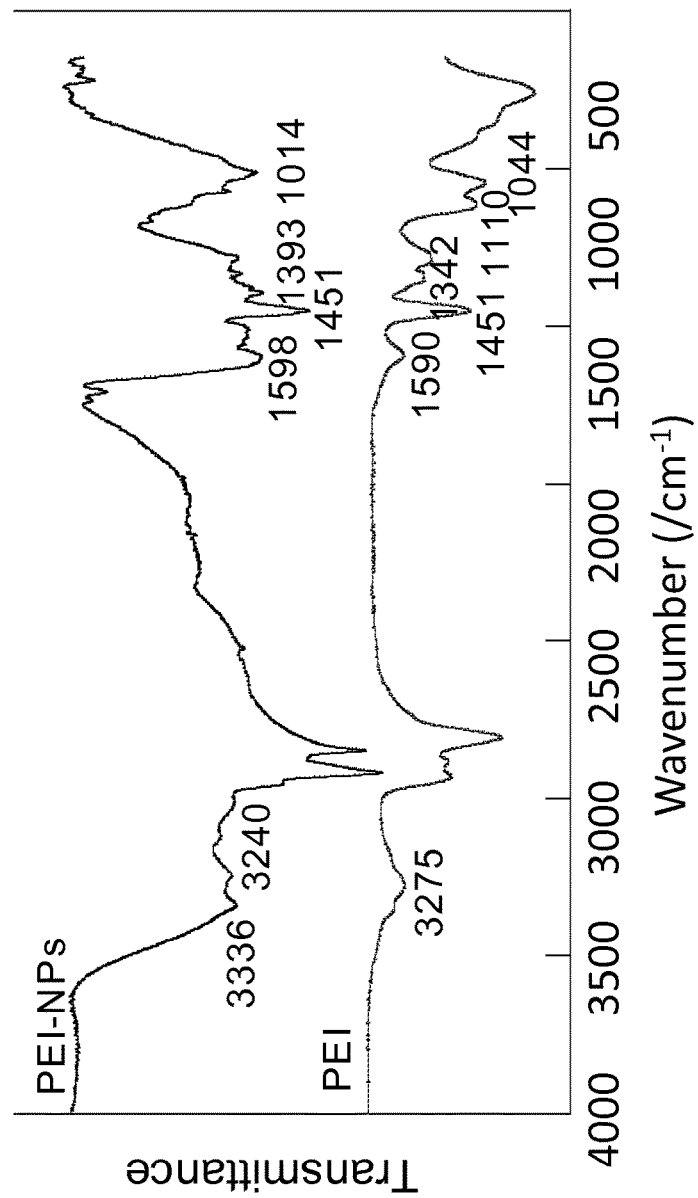
FIG. 23B is an FTIR spectrum of polyethyleneimine (PEI) attached to a nanoparticle of the disclosure (top) and polyethyleneimine (PEI) (bottom).
Figure 23C:
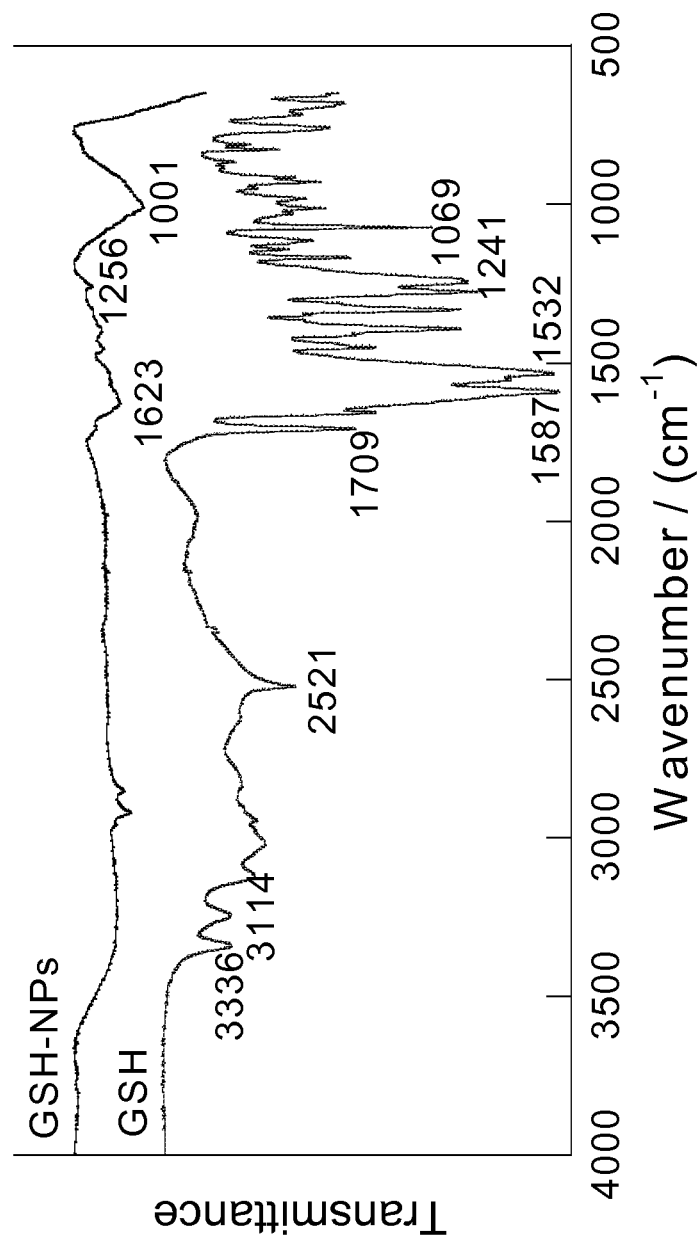
FIG. 23C is an FTIR spectrum of glutathione attached to a nanoparticle of the disclosure (top) and glutathione (bottom).
Figure 24:
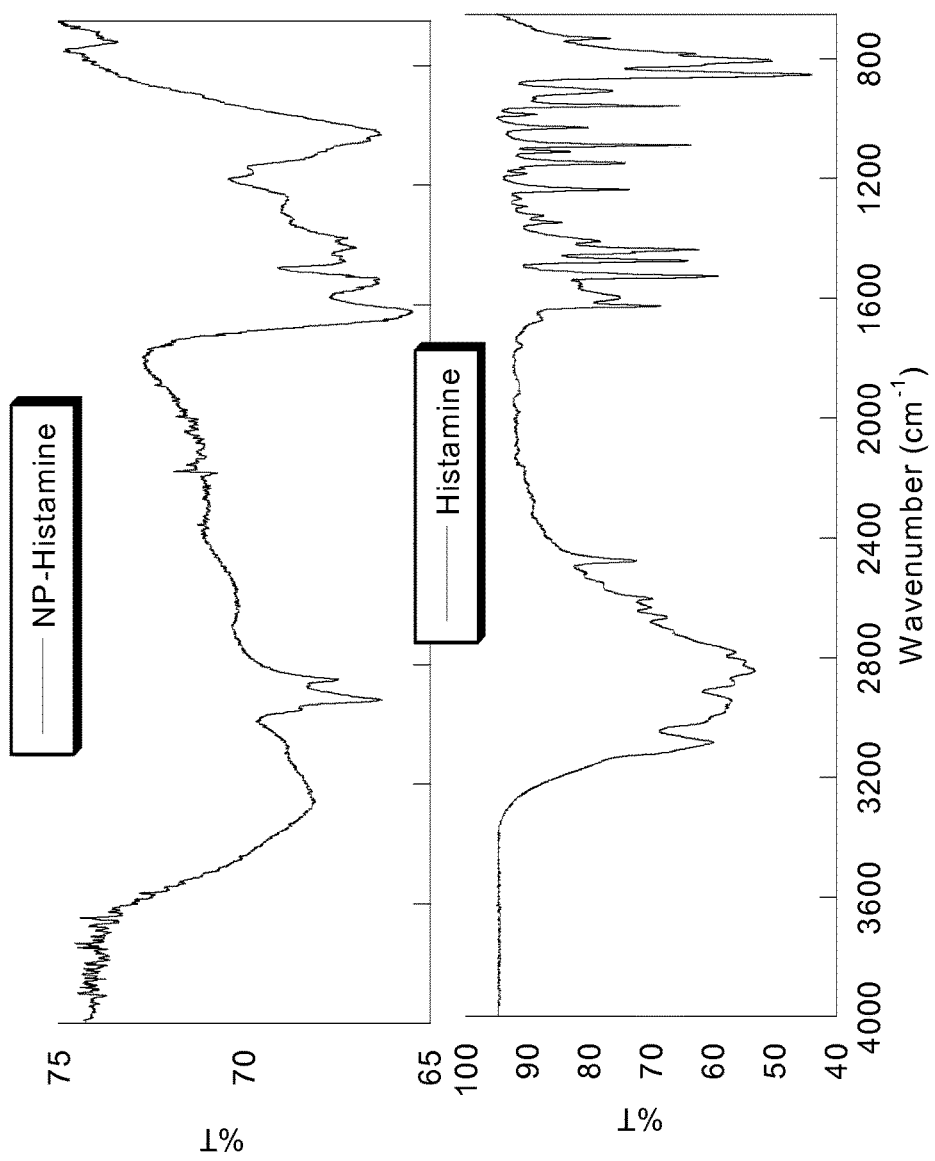
FIG. 24 is an FTIR spectrum of histamine attached to a nanoparticle of the disclosure (top) and histamine (bottom).
Figure 25:
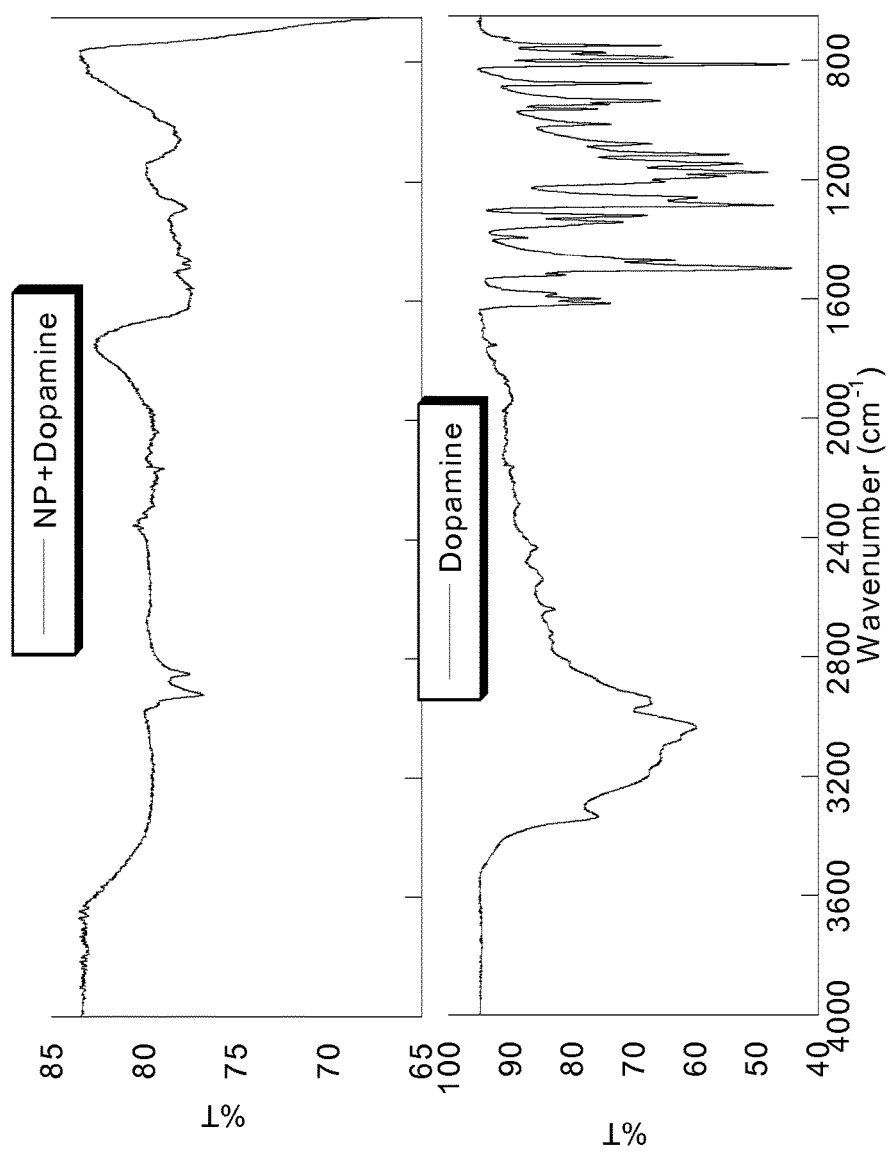
FIG. 25 is an FTIR spectrum of dopamine attached to a nanoparticle of the disclosure (top) and dopamine (bottom).
Figure 26:
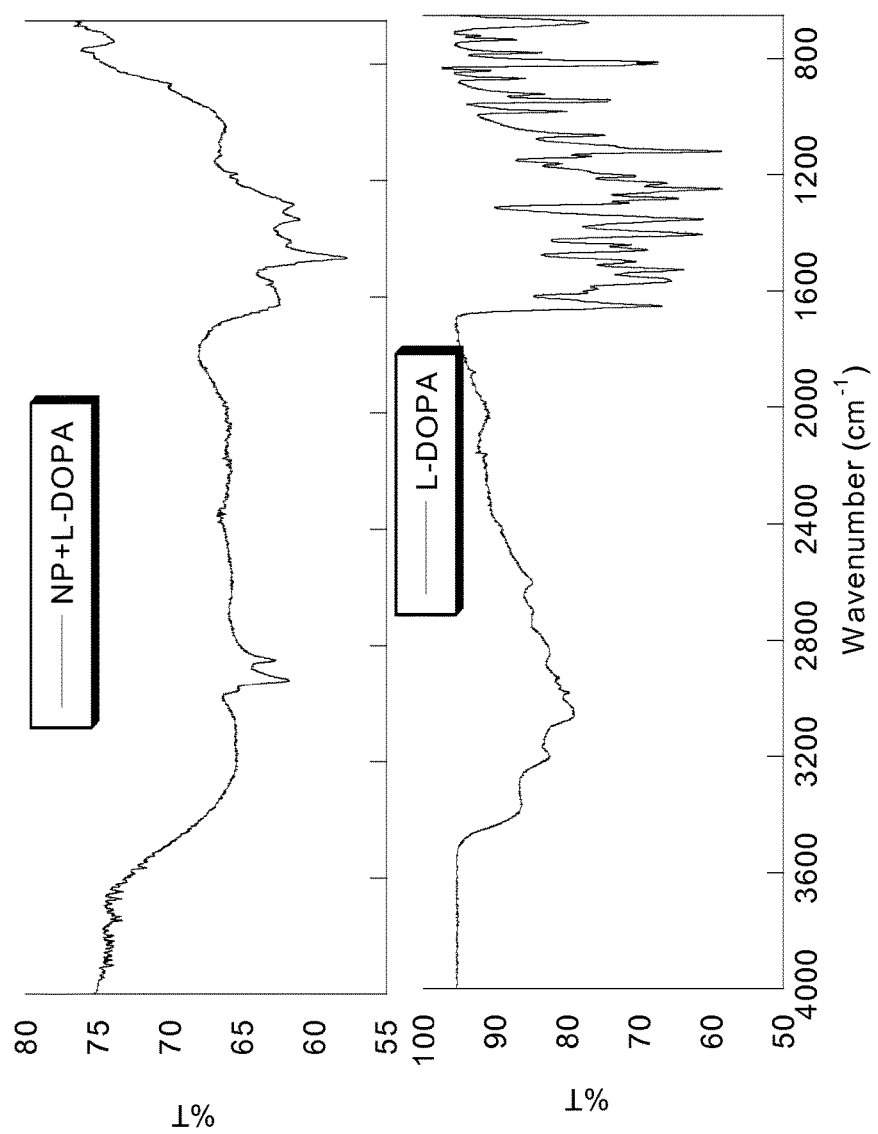
FIG. 26 is an FTIR spectrum of L-dopamine attached to a nanoparticle of the disclosure (top) and L-dopamine (bottom).

Ligands of the precursor can be different from each other such as, but not limited to, oleic acid, oleylamine, good's buffer molecules, histamine, dopamine, liquid crystals. For example the third ligand may be oleylamine resulting in nanowires as shown in FIGS. 20A and 20B.

Example 19

The nanostructures are coated with hydrophobic chains after synthesis. A subsequent ligand exchange process follows the methods in Xu et al., (2011) 27: 8990-8997 (2011) incorporated herein by reference in its entirety. Using these methods, it was possible to attach the following molecules on the surface of the nanostructure: polyacrylic acid (PAA), polyethyleneimine (PEI), glutathione (GSH), lactobionic acid (LBA), histamine, dopamine, L-DOPA, biotin. Attachment was shown by FTIR data as shown in FIGS. 23-26. These molecules provide the functional surface for further conjugation and targeting.

I claim:

1. A method of synthesizing ultrathin nanostructures, wherein the method comprises the steps of:
   (a) obtaining a metallic core-ligand complex precursor comprising a metallic moiety and a plurality of ligands attached to said metallic moiety, wherein the plurality of ligands comprises one or more ligands that are more weakly bound and one or more ligands that are more strongly-bound than the more weakly bound ligands, wherein the more weakly bound ligands are characterized in that at an incubation temperature the more weakly bound ligands dissociate and the more strongly bound ligands remain attached; and
   (b) incubating the metallic core-ligand complex precursor mix at the incubation temperature, wherein the incubation temperature is selected from the group of: from about 100° C. to about 300° C., from about 100° C. to about 200° C., from about 100° C. to about 175° C., from about 100° C. to about 150° C., about 300° C., about 250° C., about 230° C., about 225° C., about 200° C., about 180° C., about 175° C., about 170° C., about 150° C., and about 125° C.,
   wherein the incubation temperature is selected to generate a population of ultrathin nanostructures by a process of thermal displacement of some or all of the more weakly-bound ligand(s) from the metallic core, wherein the ultrathin nanostructures are a nanowhisker, a nanotube, or a nanorice having a diameter of about 4 nm or less and a longest dimension about 10 nm to 500 nm.

2. The method of claim 1, wherein the step of obtaining a metallic core-ligand complex precursor comprises mixing a metallic core, at least one ligand species, and an organic solvent, thereby forming a metallic core-ligand complex precursor:organic solvent mix.

3. The method of claim 1, wherein the diameter is about 1 nm to about 4 nm.

4. The method of claim 1, wherein the diameter is about 2 nm.

5. The method of claim 1, wherein the metallic core is selected from the group consisting of: a magnetic ferrite-based moiety selected from ferric oxide, ferrous oxide, a ferric ion, a ferrous ion, a manganese ferrite, a zinc ferrite, a copper ferrite, a chrome ferrite, a cobalt ferrite, a nickel ferrite, a non-ferrous metallic ion, and any combination thereof.

6. The method of claim 1, wherein the plurality of ligands attached to the metallic core-ligand complex comprises at least one fatty acid species, at least one non-fatty acid species, or at least one fatty acid species combined with at least one non-fatty acid species.

7. The method of claim 6, wherein the at least one fatty acid species is selected from the group consisting of: a long-chain saturated fatty acid, a long-chain mono-unsaturated fatty acid, and a long-chain unsaturated fatty acid.

8. The method of claim 6, wherein the at least one fatty acid species is selected from the group consisting of: myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, myristic acid, palmitic acid, stearic acid, arachidic acid, behenic acid, lignoceric acid, cerotic acid, eicosenoic acid, mead acid, and nervonic acid.

9. The method of claim 6, wherein the at least one fatty acid is oleic acid.

10. The method of claim 6, wherein the at least one non-fatty acid ligand is selected from the group consisting of: oleic acid, tri-N-octylphosphine oxide (TOPO), oleylamine, a Good's buffer, biotin, dopamine, histamine, a liquid crystal molecule, or any combination thereof.

11. The method of claim 1, wherein the step of obtaining a metallic core-ligand complex precursor comprises incubating a ferrite, a ferric salt, a ferrous salt, or a non-ferrous salt, with oleic acid or a salt thereof.

12. The method of claim 1, wherein the incubation temperature is selected to form a nanowhisker.

13. The method of claim 2, wherein the metallic core-ligand complex comprises a ferric oxide complexed with a plurality of oleic acid moieties, and wherein said complex is incubated in the organic solvent at about 150° C., thereby forming a population of nanowhiskers.

14. A nanostructure synthesized by a method according to claim 1.

15. A pharmaceutically acceptable composition comprising a nanostructure synthesized by a method according to claim 1 and a pharmaceutically acceptable carrier.

16. The pharmaceutically acceptable composition of claim 15, wherein the pharmaceutically acceptable composition is formulated to provide a high-contrast magnetic resonance image of a recipient animal or human subject.

17. An ultrathin nanostructure comprising a metallic core, wherein the ultrathin nanostructure is a nanowhisker, a nanotube, or a nanorice having a diameter of about 1 nm to about 4 nm and a longest dimension about 10 nm to 500 nm, and
wherein the nanostructure has a substantially reduced relaxivity compared to a nanostructure having dimensions of at least 4 nm.

18. The ultrathin nanostructure of claim 17, wherein the diameter is about 2 nm or less.

19. The ultrathin nanostructure of claim 17, wherein the metallic core is a magnetic ferrite-based moiety selected from the group consisting of: a ferric oxide, a ferrous oxide, a ferric ion, a ferrous ion, a manganese ferrite, a zinc ferrite, a copper ferrite, a chrome ferrite, a cobalt ferrite, and a nickel ferrite.

20. The ultrathin nanostructure of claim 17, wherein the ultrathin nanostructure is a nanowhisker.

21. The ultrathin nanostructure of claim 17, further comprising a biocompatible coating.

22. The ultrathin nanostructure of claim 17, further comprising a targeting ligand disposed on the surface of the ultrathin nanoparticle.

23. The ultrathin nanostructure of claim 17, further comprising at least one of the group consisting of: polyacrylic acid (PAA), polyethyleneimine (PEI), glutathione (GSH), lactobionic acid (LBA), histamine, dopamine, L-DOPA, and biotin disposed on the ultrathin nanostructure.

24. The method of claim 1, wherein the longest dimension is about 10 nm to 30 nm.

25. The ultrathin nanostructure of claim 17, wherein the longest dimension is about 10 nm to 30 nm.

* * * * *